United States Patent [19]

Melloni et al.

[11] Patent Number: 4,463,001
[45] Date of Patent: Jul. 31, 1984

[54] 6-SUBSTITUTED 6H-DIBENZO[B,D]PYRAN DERIVATIVES AND PROCESS FOR THEIR PREPARATION

[75] Inventors: Piero Melloni, Bresso; Paolo Salvadori; Pier P. Lovisolo, both of Milan, Italy

[73] Assignee: Farmitalia Carlo Erba S.p.A., Milan, Italy

[21] Appl. No.: 307,597

[22] Filed: Oct. 1, 1981

[30] Foreign Application Priority Data

Oct. 20, 1980 [GB] United Kingdom ................. 8033774
Sep. 14, 1981 [GB] United Kingdom ................. 8127718

[51] Int. Cl.$^3$ .................... A61K 31/35; C07D 311/80

[52] U.S. Cl. .................................. 424/246; 546/281; 546/279; 424/248.4; 546/278; 546/269; 424/248.51; 546/196; 546/194; 424/248.53; 546/191; 546/190; 424/248.54; 548/525; 548/519; 424/248.55; 548/374; 548/336; 424/250; 549/390; 549/391; 424/256; 424/263; 424/267; 424/269; 424/274; 424/283; 544/405; 544/378; 544/372; 544/366; 544/365; 544/360; 544/357; 544/375; 544/150; 544/141; 544/132; 544/129; 544/124; 544/121; 544/111; 544/98; 544/60; 544/58.7; 544/58.6; 544/58.4

[58] Field of Search .................. 260/345.3; 544/375, 544/405, 357, 378, 372, 366, 365, 360, 150, 141, 132, 129, 124, 121, 111, 98, 60, 58.7, 58.6, 58.4, 56; 546/196, 269, 281, 279, 278, 194, 191, 190; 424/283, 267, 263, 250, 246, 248.4, 248.53, 248.54, 248.55, 248.51, 250, 256, 269, 274; 549/390, 391; 548/525, 519, 374, 336

[56] References Cited
PUBLICATIONS

Derwent Farmdoc, 34237w, (12/73).
Derwent Farmdoc, 24298x, (11/73).
Derwent Farmdoc, 04559y, (5/75).
Derwent Farmdoc, 73604y, (1/76).

*Primary Examiner*—Nicky Chan
*Attorney, Agent, or Firm*—Murray, Whisenhunt and Ferguson

[57] ABSTRACT

The present invention relates to new 6-substituted 6H-dibenzo [b,d]pyran derivatives, to a process for their preparation and pharmaceutical and veterinary compositions containing them.

15 Claims, No Drawings

6-SUBSTITUTED 6H-DIBENZO[b,d]PYRAN DERIVATIVES AND PROCESS FOR THEIR PREPARATION

DESCRIPTION OF THE INVENTION

The compounds of this invention have the general formula (I)

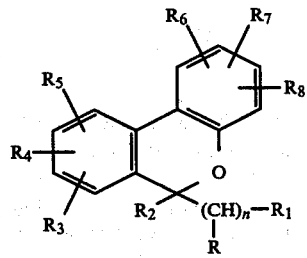

wherein
$R_1$ represents (a) cyano; (b) a carboxy or esterified carboxy group; (c)

wherein each of $R_a$ and $R_b$, being the same or different, is hydrogen or unsubstituted $C_1$-$C_6$ alkyl, or $R_a$ and $R_b$, taken together with the nitrogen atom to which they are linked, form a heterocyclic ring, optionally containing a further heteroatom chosen from oxygen, sulphur and nitrogen, and optionally substituted by $C_1$-$C_6$ alkyl or phenyl; (d)

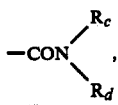

wherein each of $R_c$ and $R_d$, being the same or different, is hydrogen or $C_1$-$C_6$ alkyl unsubstituted or substituted by

wherein $R_a$ and $R_b$ are as defined above, or $R_c$ and $R_d$, taken together with the nitrogen atom to which they are linked, form a heterocyclic ring, optionally containing a further heteroatom chosen from oxygen, nitrogen and sulphur, and optionally substituted by $C_1$-$C_6$ alkyl or phenyl; (e) a saturated or unsaturated 5- or 6-membered heterocyclic ring, bound to the alkyl group or to the benzopyrane system through a carbon-carbon linkage, and containing at least a nitrogen atom and, optionally, a further heteroatom chosen from oxygen, sulphur and nitrogen, which ring is unsubstituted or optionally substituted by $C_1$-$C_6$ alkyl or phenyl;
R is hydrogen; hydroxy or amino;
n is zero, 1, 2 or 3;

$R_2$ represents hydrogen; $C_1$-$C_6$ alkyl optionally substituted by hydroxy or by a —OCO—$C_1$-$C_6$ alkyl group; or an optionally substituted phenyl group; each of $R_3$, $R_4$, $R_5$, $R_6$, $R_7$ and $R_8$, which may be the same or different, is selected from (a") hydrogen; halogen; halo-$C_1$-$C_6$ alkyl; or $C_1$-$C_6$ alkyl optionally substituted by amino; (b") amino; nitro; or

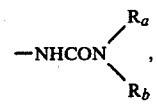

wherein $R_a$ and $R_b$ are as defined above; (c") —$OR_9$, wherein $R_9$ is hydrogen, $C_1$-$C_6$ alkyl or $C_2$-$C_6$ alkenyl; and the pharmaceutically or veterinarily acceptable salts thereof.

The invention also includes within its scope all the possible isomers, stereoisomers and optical isomers and their mixtures, and the metabolites and the metabolic precursors or bioprecursors of the compounds of formula (I).

The alkyl and alkenyl groups may be branched or straight chain groups.

A halogen atom is preferably fluorine, chlorine or bromine.

A $C_1$-$C_6$ alkyl group is preferably methyl, ethyl, propyl, isopropyl, butyl, sec-butyl or tert-butyl, preferably methyl or ethyl.

A halo-$C_1$-$C_6$ alkyl group is preferably a trihalo-$C_1$-$C_6$-alkyl group, preferably trifluoromethyl.

A $C_2$-$C_6$ alkenyl group is preferably vinyl or allyl, preferably allyl.

When $R_a$ and $R_b$ and/or $R_c$ and $R_d$, taken together with the nitrogen atom to which they are linked, form a heterocyclic ring, this may be for example an unsaturated, 5- or 6-membered heteromonocyclic ring, e.g. pyrrole, pyrazole, imidazole, dihydropyridine, dihydropyrazine, 1,4-oxazine or 1,4-thiazine or a saturated, 5- or 6-membered heteromonocyclic ring, e.g. pyrrolidine, piperidine, piperazine, morpholine or thiomorpholine. When n is other than zero, the group

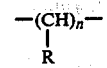

may be for example a group chosen from

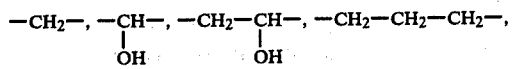

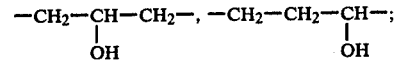

preferably it is chosen from

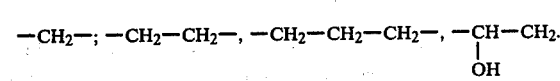

When $R_1$ is an esterified carboxy group it is preferably the group —$COOR_{10}$, wherein $R_{10}$ is

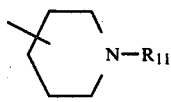

wherein $R_{11}$ is hydrogen, methyl or ethyl; or $R_{10}$ is $C_1$–$C_6$ alkyl optionally substituted by (a''')

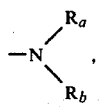

wherein $R_a$ and $R_b$ are as defined above, (b''')

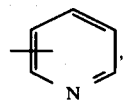

(c''') 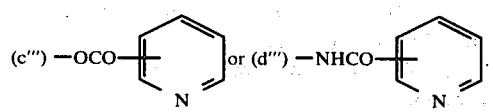

When $R_2$ represents a substituted phenyl group, the phenyl ring may be substituted preferably by one or more fluorine, chlorine, hydroxy and methoxy.

The pharmaceutically and veterinarily acceptable salts of the compounds of formula (I) include those formed with an inorganic acid, e.g. hydrochloric acid or sulphuric acid, or with an organic acid, e.g. citric, tartaric, malic, maleic, mandelic, fumaric or methanesulphonic acid, or with an inorganic base e.g. sodium, potassium, calcium or aluminium hydroxide or an alkali metal or alkaline earth metal carbonate or bicarbonate, or with an organic base, typically an organic amine, e.g. lysine, triethylamine, procaine, dibenzylamine, N-benzyl-β-phenethylamine, N,N'-dibenzyl-ethylenediamine, dehydroabietylamine, N-ethyl-piperidine, diethanolamine, N-methyl-glucamine, or tris-hydroxymethylaminomethane.

Preferred compounds of the invention are compounds of formula (I) wherein:

R is hydrogen, hydroxy or amino;

$R_1$ is a free carboxy group or an esterified carboxy group of formula —COOR'$_{10}$, wherein R'$_{10}$ is ($a^{IV}$) $C_1$–$C_4$ alkyl, unsubstituted or substituted by a group

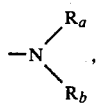

wherein $R_a$ and $R_b$ are as defined above, or by a group —(OCO)$_X$—Py, wherein X is zero or 1 and Py represents a pyridyl group; or ($b^{IV}$) an unsubstituted or methyl- or ethyl- substituted pyperidyl group; or $R_1$ is

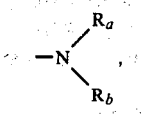

wherein $R_a$ and $R_b$ are as defined above, or

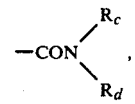

wherein $R_c$ and $R_d$ are as defined above;

$R_2$ is hydrogen, methyl, hydroxymethyl or unsubstituted phenyl;

each of $R_3$, $R_4$ and $R_5$ is, independently, hydrogen, chlorine, fluorine, trifluoromethyl, $C_1$–$C_4$ alkyl, nitro, amino or a group —O R'$_9$ wherein R'$_9$ is hydrogen or $C_1$–$C_4$ alkyl;

each of $R_6$, $R_7$ and $R_8$ is, independently, hydrogen, halogen, nitro, amino;

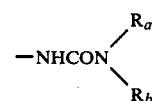

wherein $R_a$ and $R_b$ are as defined above; or a group —OR'$_9$, wherein R'$_9$ is as defined above; n is zero, 1 or 2; and the pharmaceutically or veterinarily acceptable salts thereof.

Particularly preferred compounds of the invention are the compounds of formula (I) wherein:

R is hydrogen, hydroxy or amino $R_1$ is —COOH, —COOC$_2$H$_5$, —COOCH(CH$_3$)$_2$,

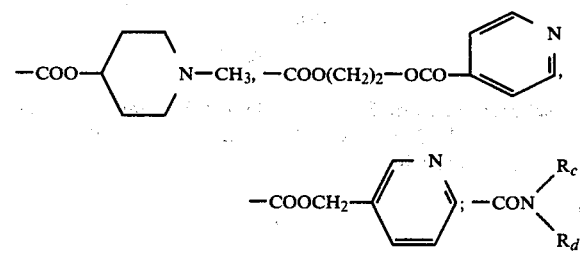

wherein $R_c$ and $R_d$ are as defined above;

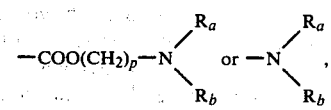

wherein p is 2 or 3 and $R_a$ and $R_b$ are as defined above;

$R_2$ is hydrogen, —CH$_3$, —CH$_2$OH or unsubstituted phenyl;

each of $R_3$, $R_4$ and $R_5$ is, independently, hydrogen, chlorine, fluorine, methyl, hydroxy, $C_1$–$C_4$ alkoxy, amino or nitro;

each of $R_6$, $R_7$ and $R_8$ is, independently, fluorine, chlorine, bromine, hydrogen, hydroxy, $C_1$–$C_4$ alkoxy, nitro, amino or

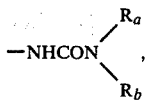

wherein $R_a$ and $R_b$ are as defined above;

n is zero, 1 or 2; and the pharmaceutically or veterinarily acceptable salts thereof.

Specific examples of compounds of the invention are the following:

6H,6-cyano-dibenzo[b,d]pyran;
6H,6-cyano-1-methoxy-dibenzo[b,d]pyran;
6H,6-cyano-2-chloro-dibenzo[b,d]pyran;
6H,6-cyano-2-fluoro-dibenzo[b,d]pyran;
6H,6-cyano-2-nitro-dibenzo[b,d]pyran;
6H,6-cyano-2-methoxy-dibenzo[b,d]pyran;
6H,6-cyano-1,10-dimethoxy-dibenzo[b,d]pyran;
6H,6-cyano-8,9,10-trimethoxy-dibenzo[b,d]pyran;
6H,6-cyano-6-methyl-dibenzo[b,d]pyran;
6H,6-cyano-6-methyl-2-chloro-dibenzo[b,d]pyran;
6H,6-cyano-6-methyl-2-fluoro-dibenzo[b,d]pyran;
6H,6-cyano-6-methyl-1,10-dimethoxy-dibenzo[b,d]pyran;
6H,6-cyano-6-methyl-8,9,10-trimethoxy-dibenzo[b,d]pyran;
6H,6-(1-piperazinyl)-dibenzo[b,d]pyran;
6H,6-(1-piperazinyl)-2-chloro-dibenzo[b,d]pyran;
6H,6-(1-piperazinyl)-2-fluoro-dibenzo[b,d]pyran;
6H,6-(1-piperazinyl)-2-nitro-dibenzo[b,d]pyran;
6H,6-(1-piperazinyl)-2-methoxy-dibenzo[b,d]pyran;
6H,6-(1-piperazinyl)-1,10-dimethoxy-dibenzo[b,d]pyran;
6H,6-(1-piperazinyl)-8,9,10-trimethoxy-dibenzo[b,d]pyran;
6H,6-ethoxycarbonyl-dibenzo[b,d]pyran;
6H,6-ethoxycarbonyl-1-methoxy-dibenzo[b,d]pyran;
6H,6-ethoxycarbonyl-2-hydroxy-dibenzo[b,d]pyran;
6H,6-ethoxycarbonyl-2-chloro-dibenzo[b,d]pyran;
6H,6-ethoxycarbonyl-6-methyl-2-chloro-dibenzo[b,d]pyran;
6H,6-ethoxycarbonyl-2-amino-dibenzo[b,d]pyran;
6H,6-ethoxycarbonyl-6-methyl-dibenzo[b,d]pyran;
6H,6-ethoxycarbonylmethyl-dibenzo[b,d]pyran;
6H,6-ethoxycarbonylmethyl-2-chloro-dibenzo[b,d]pyran;
6H,6-ethoxycarbonylmethyl-2-fluoro-dibenzo[b,d]pyran;
6H,6-ethoxycarbonylmethyl-2-nitro-dibenzo[b,d]pyran;
6H,6-ethoxycarbonylmethyl-2-amino-dibenzo[b,d]pyran;
6H,6-ethoxycarbonylmethyl-2-methoxy-dibenzo[b,d]pyran;
6H,6-ethoxycarbonylmethyl-2-hydroxy-dibenzo[b,d]pyran;
6H,6-ethoxycarbonylmethyl-1,10-dimethoxy-dibenzo[b,d]pyran;
6H,6-ethoxycarbonylmethyl-8,9,10-trimethoxy-dibenzo[b,d]pyran;
6H,6-ethoxycarbonylmethyl-6-methyl-dibenzo[b,d]pyran;
6H,6-ethoxycarbonylmethyl-6-methyl-2-chloro-dibenzo[b,d]pyran;
6H,6-ethoxycarbonylmethyl-6-methyl-2-fluoro-dibenzo[b,d]pyran;
6H,6-ethoxycarbonylmethyl-6-methyl-2-nitro-dibenzo[b,d]pyran;
6H,6-ethoxycarbonylmethyl-6-methyl-2-amino-dibenzo[b,d]pyran;
6H,6-ethoxycarbonylmethyl-6-methyl-2-methoxy-dibenzo[b,d]pyran;
6H,6-ethoxycarbonylmethyl-6-methyl-2-hydroxy-dibenzo[b,d]pyran;
6H,6-(2-ethoxycarbonylethyl)-dibenzo[b,d]pyran;
6H,6-(2-ethoxycarbonylethyl)-2-chloro-dibenzo[b,d]pyran;
6H,6-(2-ethoxycarbonylethyl)-2-fluoro-dibenzo[b,d]pyran;
6H,6-(2-ethoxycarbonylethyl)-8,9,10-trimethoxy-dibenzo[b,d]pyran;
6H,6-(2-ethoxycarbonylethyl)-6-methyl-dibenzo[b,d]pyran;
6H,6-(2-dimethylaminoethoxy-carbonyl)-dibenzo[b,d]pyran;
6H,6-(2-dimethylaminoethoxy-carbonyl)-2-chloro-dibenzo[b,d]pyran;
6H,6-(2-dimethylaminoethoxy-carbonyl)-2-fluoro-dibenzo[b,d]pyran;
6H,6-(2-dimethylaminoethoxy-carbonyl)-2-nitro-dibenzo[b,d]pyran;
6H,6-(2-dimethylaminoethoxy-carbonyl)-2-methoxy-dibenzo[b,d]pyran;
6H,6-(2-dimethylaminoethoxy-carbonyl)-2-hydroxy-dibenzo[b,d]pyran;
6H,6-(2-dimethylaminoethoxy-carbonyl)-2-amino-dibenzo[b,d]pyran;
6H,6-(2-dimethylaminoethoxy-carbonyl)-1,10-dimethoxy-dibenzo[b,d]pyran;
6H,6-(2-dimethylaminoethoxy-carbonyl)-8,9,10-trimethoxy-dibenzo[b,d]pyran;
6H,6-(2-dimethylaminoethoxy-carbonyl)-6-methyl-dibenzo[b,d]pyran;
6H,6-(2-dimethylaminoethoxy-carbonyl)-6-ethyl-dibenzo[b,d]pyran;
6H,6-(2-dimethylamino-ethoxy-carbonyl)-6-methyl-2-hydroxy-dibenzo[b,d]pyran;
6H,6-(2-dimethylamino-ethoxy-carbonyl)-6-methyl-2-amino-dibenzo[b,d]pyran;
6H,6-(2-dimethylaminoethoxy-carbonylmethyl)-dibenzo[b,d]pyran;
6H,6-(3-pyridylmethylenoxy-carbonylmethyl)-dibenzo[b,d]pyran;
6H,6-(3-pyridylmethylenoxy-carbonylmethyl)-6-methyl-dibenzo[b,d]pyran;
6H,6-carboxy-6-methyl-2-chloro-dibenzo[b,d]pyran;
6H,6-carboxy-6-methyl-2-fluoro-dibenzo[b,d]pyran;
6H,6-carboxy-6-methyl-2-nitro-dibenzo[b,d]pyran;
6H,6-carboxy-6-methyl-2-methoxy-dibenzo[b,d]pyran;
6H,6-carboxy-6-methyl-2-trifluoromethyl-dibenzo[b,d]pyran;
6H,6-carboxy-6-methyl-1,10-dimethoxy-dibenzo[b,d]pyran;
6H,6-carboxy-8,9,10-trimethoxy-dibenzo[b,d]pyran;
6H,6-carboxymethyl-dibenzo[b,d]pyran;
6H,6-carboxymethyl-1-methoxy-dibenzo[b,d]pyran;
6H,6-carboxymethyl-2-chloro-dibenzo[b,d]pyran;
6H,6-carboxymethyl-2-fluoro-dibenzo[b,d]pyran;
6H,6-carboxymethyl-2-nitro-dibenzo[b,d]pyran;
6H,6-carboxymethyl-2-methoxy-dibenzo[b,d]pyran;
6H,6-carboxymethyl-2-trifluoromethyl-dibenzo[b,d]pyran;
6H,6-carboxymethyl-8-chloro-dibenzo[b,d]pyran;
6H,6-carboxymethyl-8-fluoro-dibenzo[b,d]pyran;
6H,6-carboxymethyl-8-nitro-dibenzo[b,d]pyran;
6H,6-carboxymethyl-8-methoxy-dibenzo[b,d]pyran;

6H,6-carboxymethyl-1,10-dimethoxy-dibenzo[b,d]pyran;
6H,6-carboxymethyl-8,9,10-trimethoxy-dibenzo[b,d]pyran;
6H,6-carboxymethyl-6-methyl-dibenzo[b,d]pyran;
6H,6-(2-carboxyethyl)-dibenzo[b,d]pyran;
6H,6-(2-carboxy-ethyl)-2-chloro-dibenzo[b,d]pyran;
6H,6-(2-carboxy-ethyl)-2-fluoro-dibenzo[b,d]pyran;
6H,6-(2-carboxy-ethyl)-2-nitro-dibenzo[b,d]pyran;
6H,6-(2-carboxy-ethyl)-2-methoxy-dibenzo[b,d]pyran;
6H,6-(2-carboxy-ethyl)-1,10-dimethoxy-dibenzo[b,d]pyran;
6H,6-(2-carboxy-ethyl)-8,9,10-trimethoxy-dibenzo[b,d]pyran;
6H,6-amino-methyl-dibenzo[b,d]pyran;
6H,6-amino-methyl-2-chloro-dibenzo[b,d]pyran;
6H,6-aminomethyl-2-fluoro-dibenzo[b,d]pyran;
6H,6-aminomethyl-2-methoxy-dibenzo[b,d]pyran;
6H,6-aminomethyl-2-hydroxy-dibenzo[b,d]pyran;
6H,6-aminomethyl-1,10-dimethoxy-dibenzo[b,d]pyran;
6H,6-aminomethyl-8,9,10-trimethoxy-dibenzo[b,d]pyran;
6H,6-(2-methylamino-ethyl)-dibenzo[b,d]pyran;
6H,6-(3-methylamino-propyl)-dibenzo[b,d]pyran;
6H,6-(3-methylamino-propyl)-1-methoxy-dibenzo[b,d]pyran;
6H,6-(4-piperidinyl)-dibenzo[b,d]pyran;
6H,6-(1-hydroxy-2-tert-butylamino-ethyl)-dibenzo[b,d]pyran;
6H,6-(1-hydroxy-2-tert-butylamino-ethyl)-2-chloro-dibenzo[b,d]pyran;
6H,6-(1-hydroxy-2-tert-butylamino-ethyl)-2-methoxy-dibenzo[b,d]pyran;
6H,6-(1-hydroxy-2-tert-butylamino-ethyl)-1,10-dimethoxydibenzo[b,d]pyran;
6H,6-(1-hydroxy-2-tert-butylamino-ethyl)-8,9,10-trimethoxydibenzo[b,d]pyran,
and the pharmaceutically or veterinarily acceptable salts thereof.

The compounds of the present invention may be prepared by a process comprising:

(a) reacting a compound of formula (II)

(II)

wherein $R_{12}$ is a halogen atom or a hydroxy group; $R'_2$ is hydrogen, unsubstituted $C_1-C_6$ alkyl or an optionally substituted phenyl group and $R_3$, $R_4$, $R_5$, $R_6$, $R_7$ and $R_8$ are as defined above, with an alkali metal cyanide or with a $C_1-C_6$-alkylsilylcyanide or with an amine of formula

wherein $R_a$ and $R_b$ are as defined above, so obtaining a compound of formula (I), wherein n is zero; $R_1$ is —CN or

wherein $R_a$ and $R_b$ are as defined above; $R_2$ is hydrogen, unsubstituted $C_1-C_6$ alkyl or an optionally substituted phenyl group; and $R_3$, $R_4$, $R_5$, $R_6$, $R_7$ and $R_8$ are as defined above; or (b) reacting a compound of formula (III)

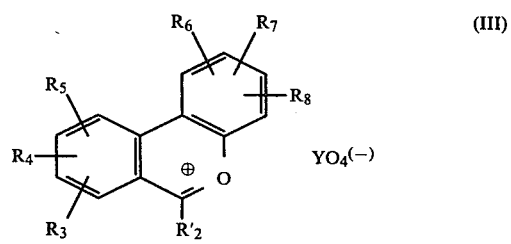
(III)

wherein Y is an halogen atom; $R'_2$ is hydrogen, unsubstituted $C_1-C_6$ alkyl or an optionally substituted phenyl group and $R_3$, $R_4$, $R_5$, $R_6$, $R_7$ and $R_8$ are as defind above, with an alkali metal cyanide, so obtaining a compound of formula (I), wherein n is zero; $R_2$ is hydrogen, unsubstituted $C_1-C_6$ alkyl or an optionally substituted phenyl group; $R_1$ is —CN and $R_3$, $R_4$, $R_5$, $R_6$, $R_7$ and $R_8$ are as defined above; or (c) reacting a compound of formula (II), wherein $R_{12}$ is hydroxy; $R'_2$ is hydrogen, unsubstituted $C_1-C_6$ alkyl or an optionally substituted phenyl group; $R_3$, $R_4$, $R_5$, $R_6$, $R_7$ and $R_8$ are as defined above, with a Wittig reagent of formula (IV)

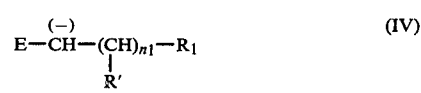
(IV)

wherein
$R_1$ is as defined above; $n_1$ is zero, 1 or 2; E is $(C_6H_5)_3P-$ or a $$\overset{O}{\underset{(R_eO)_2P-}{\uparrow}}$$

group, where each of $R_e$ may be independently $C_1-C_6$ alkyl or phenyl and $R'$ is hydrogen or amino; so obtaining a compound of formula (I), wherein n is 1, 2 or 3; R is hydrogen or amino, wherein when R is amino, it is never linked to the α-carbon atom bound at the 6-position of the benzopyrane system; $R_2$ is hydrogen, unsubstituted $C_1-C_6$ alkyl or an optionally substituted phenyl group; $R_1$, $R_3$, $R_4$, $R_5$, $R_6$, $R_7$ and $R_8$ are as defined above; or (d) cyclizing a compound of formula (V)

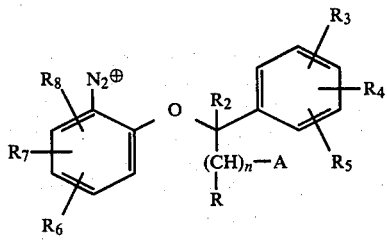

(V)

wherein A is $R_1$, where $R_1$ is as defined above, or a protected carboxy group and n, R, $R_2$, $R_3$, $R_4$, $R_5$, $R_6$, $R_7$ and $R_8$ are as defined above and removing the protecting group(s), when present, so obtaining a compound of formula (I), wherein n, R, $R_1$, $R_2$, $R_3$, $R_4$, $R_5$, $R_6$, $R_7$ and $R_8$ are as defined above, or (e) cyclizing a compound of formula (VI)

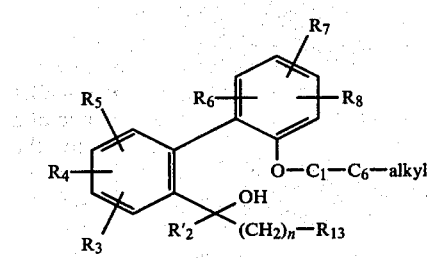

(VI)

wherein $R'_2$ is hydrogen, unsubstituted $C_1$-$C_6$ alkyl or an optionally substituted phenyl group; $R_{13}$ is as $R_1$ defined above under (a), (b) or (e), and n, $R_3$, $R_4$, $R_5$, $R_6$, $R_7$ and $R_8$ are as defined above, so obtaining a compound of formula (I), wherein R is hydrogen; and, if $R_{13}$ is as $R_1$ defined above under (a) or (b), $R_1$ is a free carboxy group, or, if $R_{13}$ is as $R_1$ defined above under (e) also $R_1$ is as defined above under (e); $R_2$ is hydrogen, unsubstituted $C_1$-$C_6$ alkyl or an optionally substituted phenyl group; and n, $R_3$, $R_4$, $R_5$, $R_6$, $R_7$ and $R_8$ are as defined above; and, if desired, converting a compound of formula (I) into another compound of formula (I), and/or, if desired, salifying a compound of formula (I) or obtaining a free compound of formula (I) from a salt thereof and/or, if desired, resolving a mixture of isomers into the individual isomers.

When in the compounds having the formulae (II), (III), (IV), (V) and (VI) free amino, carboxy or hydroxy groups are present, the amino, carboxy and hydroxy groups may be protected, if necessary, in a conventional manner, before the reaction takes place.

Amino and carboxy protecting groups may be, for example, the protecting groups usually employed in the chemistry of peptides. Examples of amino protecting groups are formyl, an optional halo-substituted $C_2$-$C_6$ aliphatic acyl, preferably chloroacetyl or dichloroacetyl, tert-butoxycarbonyl, p-nitrobenzyloxycarbonyl or trityl.

Examples of carboxy protecting groups are tert-butyl, benzhydryl, p-methoxybenzyl, p-nitrobenzyl, trityl, trialkylsilyl group, or a carboxy group may be protected in the form of a oxazolinyl group.

The hydroxy groups may be protected, for example, by a formyl, acetyl, chloroacetyl, dichloroacetyl, trifluoroacetyl, tetrahydropyranyl, trityl or silyl group, preferably trimethylsilyl or dimethyl-tert.butyl silyl.

The amino, carboxy and hydroxy protecting groups are then removed at the end of the reaction, usually in a known manner. For example, when the amino protecting group is the monochloroacetyl group, it may be removed by treatment with thiourea; the formyl and the trifluoroacetyl groups may be removed by treatment with potassium carbonate in aqueous methanol and the trityl group by treatment with formic or trifluoroacetic acid.

The carboxy protecting groups, for example, may be removed by mild acid hydrolysis or by catalytic hydrogenation, e.g. with Pd/C at room pressure.

The hydroxy protecting groups, for instance, may be removed by mild reaction conditions, e.g. acid hydrolysis.

When in the compounds of formula (II) $R_{12}$ is halogen, the halogen may be chlorine, bromine or iodine, preferably chlorine, and the reaction may be performed with an alkaline, e.g. sodium or potassium, cyanide, preferably potassium cyanide. When in the compounds of formula (II) $R_{12}$ is hydroxy, the reaction is preferably performed with a $C_1$-$C_6$ alkylsilylcyanide, preferably trimethylsilylcyanide, and in the presence of a suitable catalyst, for example, $ZnI_2$ in an inert solvent, such as benzene or toluene.

The reaction of a compound of formula (II) wherein $R_{12}$ is halogen with an alkali metal cyanide may be carried out in a suitable organic solvent, e.g. dimethylformamide, dimethylacetamide, dioxane or, preferably, in an aqueous solvent, e.g. a mixture of dimethylformamide or dimethylacetamide and water, at temperatures ranging from about 0° C. to the solvent reflux temperature, preferably at room temperature. The compounds of formula (II) wherein $R_{12}$ is hydroxy are, preferably, the starting materials for obtaining compounds of formula (I), wherein $R_1$ is

wherein $R_a$ and $R_b$ are as defined above, according to process (a). The reaction of a compound of formula (II), wherein $R_{12}$ is hydroxy with an amine of formula

wherein $R_a$ and $R_b$ are as defined above, is preferably carried out in an excess of the amine or in a solvent, such as, dimethylacetamide, N-methylpyrrolidone, benzene, toluene or mixtures thereof, at temperatures ranging from about 50° C. to about 150° C.

When in the compound of formula (III) Y is a halogen atom, the halogen may be bromine, iodine or chlorine, preferably chlorine.

The reaction of a compound of formula (III) with an alkali metal e.g. sodium or potassium, cyanide, preferably potassium cyanide, may be effected in an inert organic solvent, e.g. benzene, toluene, xylene, dioxane, preferably benzene, in the presence of a suitable catalyst, for example a crown ether, preferably a 18-crown-6-ether, at temperatures ranging from about 0° C. to the solvent reflux temperature, preferably at room temperature.

The reaction of a compound of formula (II) with a compound of formula (IV) may be performed in an anhydrous organic solvent, for example diethyl ether, benzene, toluene, xylene or n-hexane, either under cooling or at temperatures ranging from about 0° C. to the reflux temperature of the reaction mixture, preferably at room temperature.

When in the compound of formula (V) A is a protected carboxy group it is protected, for example, through one of the protecting groups indicated above, i.e. tert-butyl, benzhydryl, p-methoxybenzyl, p-nitrobenzyl, trityl, trialkylsilyl or as an oxazolinyl group. In the latter case A represents, preferably a group of formula

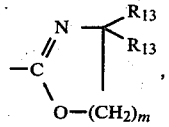

wherein each of the $R_{13}$ groups is, independently, hydrogen or $C_1$-$C_4$ alkyl, preferably methyl and m is 1 or 2.

The cyclization of a compound of formula (V) may be carried out with a suitable cyclizing agent, for example $Cu(NO_3)_2 \cdot 3H_2O/Cu_2O$ in aqueous or alcoholic, e.g. ethanolic, solvent, at temperatures ranging from about 0° C. to about 50° C., preferably from 5° C. to 30° C.

The subsequent removal of the protecting groups possibly present may be carried out by a conventional way, e.g. as reported above. In particular when in a compound of formula (V), A is a protected carboxy group of formula

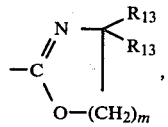

wherein $R_{13}$ and m are as defined above, the protecting group may be removed in the presence of a suitable acid, for example an inorganic acid, i.e. hydrochloric or sulphuric acid, or an organic acid, i.e. oxalic acid, in aqueous medium at temperatures ranging from the room temperature to the reflux temperature of the reacting mixture, for reaction times ranging from 1 to 12 hours, thus giving a compound of formula (I) wherein $R_1$ is a free carboxy group.

The same process, when carried out using a $C_1$-$C_6$ aliphatic alcohol as solvent, e.g. using a 5-7% solution of sulphuric acid in the appropriate $C_1$-$C_6$ aliphatic alcohol, leads to a compound of formula (I) wherein $R_1$ is a $C_2$-$C_7$ alkoxycarbonyl group. The cyclization of a compound of formula (VI) may be, for example, carried out by dissolving a compound of formula (VI) into an aqueous saturated solution of a halogenic acid, preferably hydrobromic acid, and keeping the temperature of the reacting mixture comprised between about 60° C. and the boiling point of the reacting mixture.

The optional conversion of a compound of formula (I) into another compound of formula (I) may be carried out by known methods and free amino, carboxy or hydroxy groups, when present, may be protected, if necessary, in a conventional way as reported above, before the reaction takes place and then removed at the end of the reaction in a known manner, as reported above.

(a') For example a compound of formula (I) wherein $R_1$ is cyano, R, $R_2$, $R_3$, $R_4$, $R_5$, $R_6$, $R_7$, $R_8$ and n are as defined above, may be converted into the corresponding compound of formula (I) wherein $R_1$ is —COOH, in a conventional manner, for example by alkaline hydrolysis, e.g. with KOH or NaOH in a hydroalcoholic solution, preferably with KOH in aqueous ethanol solution, at temperatures ranging from about 30° C. to the solvent reflux temperature, followed by acidification.

(b') A compound of formula (I) wherein $R_1$ is a free carboxy group may be converted into a compound of formula (I) wherein $R_1$ is the group —$COOR_{10}$, wherein $R_{10}$ is as defined above, by a conventional method, for example by reacting the alkali metal salt of the acid with an alkyl halide, in an inert solvent, such as, e.g. acetone, dioxane, dimethylformamide or hexamethylphosphorotriamide at a temperature ranging from about 0° C. to about 100° C., or by reacting the acid with an alcohol of formula $R_{10}$ —OH wherein $R_{10}$ is as defined above, in the presence of a suitable acid catalyst, e.g. HCl. Alternatively the esterification of a compound of formula (I) may be effected (a) converting the compound of formula (I) wherein $R_1$ is a carboxy group into the corresponding halocarbonyl, preferably chlorocarbonyl, derivative, by reaction, e.g. with the desired acid halide, for example oxalyl chloride, thionyl chloride, $PCl_3$, $PCl_5$ or $POCl_3$, either in the absence of a solvent or in an inert organic solvent, e.g. benzene, toluene, xylene, dioxane, dichloroethane, methylene chloride, or tetrahydrofuran, at a temperature preferably from about 0° C. to about 120° C.; and then (b) reacting the obtained halocarbonyl derivative with the suitable alcohol of formula $R_{10}$—OH, wherein $R_{10}$ is as defined above, in a solvent which may be the same alcohol or in an inert solvent, e.g. benzene, toluene, xylene, dioxane, dichloroethane, methylene chloride, or tetrahydrofuran, at a temperature preferably from about 0° C. to about 60° C., preferably in the presence of a base, e.g. triethylamine.

(c') A compound of formula (I) wherein $R_1$ is a carboxy group or an esterified carboxy group may be converted into a compound of formula (I), wherein $R_1$ is

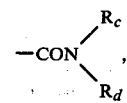

in which $R_c$ and $R_d$ are as defined above, by conventional method, for example by reacting the acid, or a reactive derivative thereof, e.g. an acyl halide, preferably chloride or a mixed anhydride, or a $C_1$-$C_6$ aliphatic ester thereof with an amine of formula

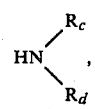

wherein $R_c$ and $R_d$ are as defined above, or a derivative thereof, e.g. an amine salt. The reaction may be performed either at room temperature or under cooling, preferably from about −50° C. to about 40° C. in a suitable solvent, e.g. acetone, dioxane, tetrahydrofuran, acetonitrile, methylene chloride, benzene, toluene, or in a mixture of water and a solvent miscible with water and, if necessary, in the presence of a base, e.g. sodium bicarbonate or potassium bicarbonate, or in the presence of an acid acceptor, e.g. propylene oxide. In particular when a free acid or a salt thereof is reacted with ammonia or the appropriate amine, the reaction is performed in the presence of a condensing agent, e.g. N,N'-dicyclohexylcarbodiimide.

(d') A compound of formula (I) wherein $R_1$ is a group

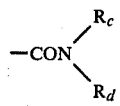

or a group —COOR$_{10}$, wherein $R_c$, $R_d$ and $R_{10}$ have the meanings reported above, may be converted into a compound of formula (I) wherein $R_1$ is —COOH by hydrolysis, e.g. basic hydrolysis, using for example, sodium or potassium hydroxide, in a solvent, such as, e.g., water or a lower aliphatic alcohol, and operating at a temperature ranging from the room temperature to about 150° C. and then acidifying; or acid hydrolysis, for example, in a solvent, such as, water, or mixtures of aliphatic alcohol or dioxane with water, operating at a temperature ranging from the room temperature to the reflux temperature; the same reaction may be also carried out e.g. by treatment with a lithium halide, preferably lithium bromide in a suitable solvent, e.g. dimethylsulphoxide, hexamethylenphosphortriamide or dimethylformamide, preferably in dimethylformamide at a temperature higher than 50° C.

In particular a compound of formula (I) wherein —COOR$_{10}$ represents a t-butoxycarbonyl group may be converted into a compound of formula (I) wherein $R_1$ is a free carboxy group e.g. by treatment with trifluoroacetic acid either in the absence of solvents or in the presence of an inert organic solvent selected e.g. from the group consisting of benzene, toluene, dioxane at a temperature ranging from about 0° C. to about 50° C. or also by treatment e.g. with trimethylsilyliodide in an inert organic solvent, preferably tetrachloromethane, according to the procedure described in J. Am. Chem. Soc. 1977, 99, 968.

(e') A compound of formula (I), wherein $R_1$ is a cyano group; R is as defined above and n is zero, 1 or 2, may be converted into another compound of formula (I), wherein $R_1$ is an amino group; n is 1 and R is hydrogen or n is 2 or 3, respectively, and R is as defined above, by reducing the cyano group in a conventional way, for example by one of the methods reported in "Catalytic Hydrogenation in Organic Synthesis" by P. N. Rylander, Academic Press 1979, page 138.

(f') Alternatively, (1) a compound of formula (I), wherein $R_1$ is a cyano group, R is as defined above, n is zero, 1 or 2, may be converted into another compound of formula (I), wherein $R_1$ is an amino group, n is 1 and R is hydrogen or n is 2 or 3 and R is as defined above; or (2) a compound of formula (I), wherein $R_1$ is a group

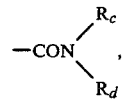

wherein $R_c$ and $R_d$ are as $R_a$ and $R_b$, wherein $R_a$ and $R_b$ are as defined above, n is zero, 1 or 2 and R is as defined above, may be converted into another compound of formula (I), wherein $R_1$ is a group

wherein $R_a$ and $R_b$ are as defined above, n is 1 and R is hydrogen or n is 2 or 3 and R is as defined above. Both the cyano or the amide groups may be reduced through a suitable reducing agent, such as LiAlH$_4$, BH$_3$, sodium dimethoxy-ethoxy-aluminium hydride (RED-AL), in organic solvents, e.g. tetrahydrofuran, diethylether, diglyme, benzene, toluene and at reaction temperatures ranging from the room temperature to the solvents' reflux temperatures.

(g') A compound of formula (I), wherein $R_1$ is an unsaturated heterocyclic ring as defined above under (e), may be coverted into another compound of formula (I), wherein $R_1$ is the respective saturated heterocyclic ring as defined above under (e), by reduction through known methods, for example those reported in "Catalytic Hydrogenation in Organic Synthesis" by P. N. Rylander, Academic Press 1979, page 213.

(h') A compound of formula (I), wherein $R_1$ is —COOH or an esterified carboxy group, n is zero, 1 or 2 and R is hydrogen, may be converted into another compound of formula (I), wherein $R_1$ is —CN or —COOH, n is 1, 2 or 3 and R is hydroxy, that is, for example, a compound of formula (I), wherein the group

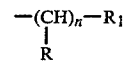

is —CH$_2$—COOH, may be transformed into another compound of formula (I), wherein the same group is —CH$_2$—CHOH—COOH. This conversion may be, for example, carried out by reducing the carboxy group or the esterified carboxy group to an aldehyde group through conventional methods well known in literature, e.g. J.O.C. 1976, 41, 3512; Chem. Comm. 1974, 45; Chem. Ber. 1970, 103, 2984; Chem. Comm. 1978, 354; and J. Chem. Soc. Perkin Trans. I (1980), (1), 27; and converting the aldehyde derivatives so obtained first into the respective cyanohydrins, that is a compound of formula (I), wherein $R_1$ is —CN and R is hydroxy, and then converting the latter into the respective hydroxy acid derivatives. Also these reactions may be carried out by following conventional methods well known in the art.

(i') A compound of formula (I), wherein $R_1$ is a carboxy or esterified carboxy group, n is zero, 1 or 2 and R is hydrogen, may be converted into another compound of formula (I) wherein $R_1$ is

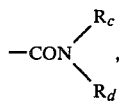

wherein $R_c$ and $R_d$ are as defined above, n is 1, 2 or 3 and R is hydroxy, that is, for example, a compound of formula (I), wherein the group

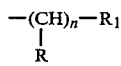

is —CH$_2$—COOH, may be transformed into another compound of formula (I), wherein the same group is

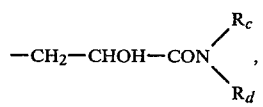

wherein $R_c$ and $R_d$ are as defined above.

This conversion may be, for example, carried out by converting, through conventional methods, the hydroxy acids, obtained according to the preceding process (h'), into the respective amides. Some of the amides obtained according to this process may be used as starting compounds for the conversion described under (f'), where amides are converted into amines.

(j') A compound of formula (I), wherein R$_1$ is a carboxy or esterified carboxy group, n is zero, or 1 and R is hydrogen, may be converted into another compound of formula (I), wherein R$_1$ is —NH$_2$, n is 2 or 3 and R is hydroxy, that is, for example, a compound of formula (I), wherein the group

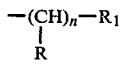

is —CH$_2$—COOH, may be transformed into another compound of formula (I), wherein the same group is

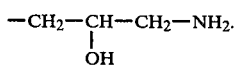

This conversion may be, for example, carried out by converting, through known methods, the cyanohydrin intermediates, obtained according to the preceding interconversion process (h'), into the respective amines.

(k') A compound of formula (I), wherein R$_2$ is hydrogen, n is zero, R$_1$ is as defined above under (a), (b), (d) or (e) and R$_3$, R$_4$, R$_5$, R$_6$, R$_7$ and R$_8$ are as defined above may be converted into the corresponding compound of formula (I) wherein R$_2$ is methyl or ethyl optionally substituted by hydroxy, by following known methods. For example a compound of formula (I) wherein R$_2$ is hydrogen, may be transformed into a compound of formula (I) wherein R$_2$ is methyl or ethyl by reaction with methyl or ethyl halide, preferably iodide, in the presence of NaH or a similar strong base and in a suitable anhydrous solvent, i.e. dimethylformamide, dioxane, toluene, xylene or dimethylsulphoxide, preferably dimethylformamide.

(l') Alternatively, a compound of formula (I), wherein R$_2$ is hydrogen, n is zero, R$_1$ is as defined above under (a), (b), (d) or (e) and R$_3$, R$_4$, R$_5$, R$_6$, R$_7$ and R$_8$ are as defined above, may be transformed into the corresponding compound of formula (I) wherein R$_2$ is methyl or ethyl substituted by a hydroxy group by reaction, for example, with formaldehyde or with a cyclic or linear polymer thereof, e.g. trioxymethylene, or with acetaldehyde, in a suitable solvent, e.g. dimethylsulphoxide at a temperature ranging from approximately the room temperature to about 100° C., for reaction times from about 2 to 12 hours, and in the presence of a base, such as sodium methoxide or potassium tert-butoxide.

(m') A compound of formula (I), wherein n is zero, 1 or 2; R is hydrogen; R$_1$ is a carboxy group; and R$_2$, R$_3$, R$_4$, R$_5$, R$_6$, R$_7$ and R$_8$ are as defined above may be converted into another compound of formula (I), wherein n is 1, 2 or 3, respectively; R is hydrogen; R$_1$ is a free or esterified carboxy group or

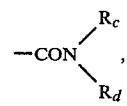

wherein $R_c$ and $R_d$ are as defined above and R$_2$, R$_3$, R$_4$, R$_5$, R$_6$, R$_7$ and R$_8$ are as defined above. Also this conversion may be carried out by following known methods, for example an Arndt-Eistert synthesis.

(n') A compound of formula (I), wherein one or more of R$_3$, R$_4$, R$_5$, R$_6$, R$_7$ and R$_8$ are hydrogen may be converted into the corresponding compound of formula (I), wherein one or more of R$_3$, R$_4$, R$_5$, R$_6$, R$_7$ and R$_8$ are halogen by halogenation. In particular, for example, a compound of formula (I) wherein one or more of R$_3$, R$_4$, R$_5$, R$_6$, R$_7$ and R$_8$ are hydrogen may be transformed into a compound of formula (I) wherein one or more of R$_3$, R$_4$, R$_5$, R$_6$, R$_7$ and R$_8$ are chlorine by reaction with a suitable chlorinating agent, for instance with SO$_2$Cl$_2$ in an inorganic solvent, e.g. CH$_2$Cl$_2$ or CHCl$_3$, or by following other well known methods, for example those described in J.O.C., 1970, 35, 719 or Synthesis 1979, 417.

(o') A compound of formula (I), wherein one or more of R$_3$, R$_4$, R$_5$, R$_6$, R$_7$ and R$_8$ are hydrogen, may be transformed into another compound of formula (I), wherein one or more of R$_3$, R$_4$, R$_5$, R$_6$, R$_7$ and R$_8$ is —NO$_2$ by conventional methods, for example by treatment with nitric acid in an appropriate solvent which may be, for instance, acetic acid, acetic anhydride or concentrated sulphuric acid, at temperatures ranging from the room temperature to about 70° C.

(p') A compound of formula (I) wherein one or more of R$_3$, R$_4$, R$_5$, R$_6$, R$_7$ and R$_8$ is —NO$_2$ and the others are hydrogen may be transformed into a compound of formula (I) wherein one or more of R$_3$, R$_4$, R$_5$, R$_6$, R$_7$ and R$_8$ is —NH$_2$ and the others are hydrogen by conventional methods, for example by hydrogenation in the presence of a suitable catalyst, e.g. Pd/C or PtO$_2$/C, and in a solvent such as, e.g., an aliphatic alcohol, acetic acid, tetrahydrofuran or dimethylformamide, or by treatment with SnCl$_2$, as reported in J. Med. Chem. 1978, 21, 621 or by treatment with TiCl$_3$ in a suitable solvent, e.g. benzene, water, ethyl acetate, or a mixture thereof, or by treatment with NaBH$_4$ or KBH$_4$ in the presence of metal catalysts as reported, e.g., in Tetr. Lett. 1969, 4555. Simultaneous reduction of other reducible groups possibly present can be avoided, if undesired, by using selective reaction conditions.

(q') A compound of formula (I), wherein one or more of $R_3$, $R_4$, $R_5$, $R_6$, $R_7$ and $R_8$ is an amino group may be transformed into another compound of formula (I), wherein one or more of $R_3$, $R_4$, $R_5$, $R_6$, $R_7$ and $R_8$ is a hydroxy group by following known methods, for example by treatment with an alkali metal nitrite, i.e. $NaNO_2$ and a mineral acid, e.g. HCl or $H_2SO_4$ at temperatures ranging from the room temperature to 70° C., preferably from the room temperature to 50° C.

(r') A compound of formula (I) wherein $R_2$ is $C_1$–$C_6$ alkyl substituted by hydroxy may be converted into the corresponding compound wherein $R_2$ is $C_1$–$C_6$ alkyl substituted by a group —O—CO—$C_1$–$C_6$-alkyl by acylation, e.g. by treatment with the appropriate acyl halide or the appropriate anhydride operating in a solvent such as, for instance, methylene chloride, chloroform or tetrahydrofuran at a temperature varying from about −10° C. to the room temperature.

(s') Vice-versa a compound of formula (I) wherein $R_2$ is $C_1$–$C_6$ alkyl substituted by a group —O—CO—$C_1$–$C_6$-alkyl may be converted into the corresponding compound wherein $R_2$ is $C_1$–$C_6$ alkyl substituted by hydroxy by hydrolysis, especially basic hydrolysis with hydroalcoholic solutions of NaOH or KOH at the reflux temperature of the used alcohol.

(t') A compound of formula (I), wherein one or more of $R_3$, $R_4$, $R_5$, $R_6$, $R_7$ and $R_8$ is a $C_1$–$C_6$ alkoxy group may be transformed into another compound of formula (I), wherein one or more of $R_3$, $R_4$, $R_5$, $R_6$, $R_7$ and $R_8$ is a hydroxy group by following known methods, for example, either by treatment with $BBr_3$ in anhydrous $CH_2Cl_2$ or other suitable solvents at temperatures ranging from about −30° C. to the room temperature, or by treatment with concentrated HBr in water at temperatures ranging from the room temperature to the reflux temperature.

Also the optional salification of a compound of formula (I) as well as the conversion of a salt into the free compounds and the separation of a mixture of isomers into the single isomers may be carried out by conventional methods. For example the separation of optical isomers may be carried out by salification with an optically active base or acid and by subsequent fractional crystallization of the diastereoisomeric salts followed by recovering of the optically active isomeric acids or, respectively, bases.

The separation of a mixture of cis- and trans-geometric isomers may be carried out for example by fractional crystallization or by chromatography.

A compound of formula (II), wherein $R_3$, $R_4$, $R_5$, $R_6$, $R_7$ and $R_8$ are as defined above, $R'_2$ is hydrogen and $R_{12}$ is hydroxy may be obtained by reducing a compound of formula (VII)

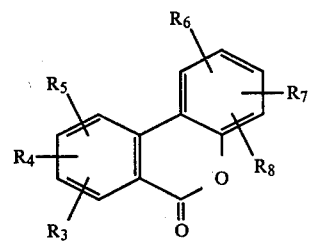

(VII)

wherein $R_3$, $R_4$, $R_5$, $R_6$, $R_7$ and $R_8$ are as defined above, following the known methods of the organic chemistry, for example by treatment with diisobutylaluminiumhydride (DIBAH), as reported in Synth., 1975, 10, 617, in Tetr. Lett., 1976, 3279; or with sodium dimethoxy-ethoxy-aluminium hydride (RED-AL), as reported in Synthesis, 1976, 8, 526, or with $LiAlH_4$, as reported in Helv. Chim. Acta, 1957, 40, 1034. A compound of formula (II), wherein $R_3$, $R_4$, $R_5$, $R_6$, $R_7$ and $R_8$ are as defined above, $R'_2$ is methyl, ethyl or an optionally substituted phenyl group and $R_{12}$ is hydroxy, may be obtained by reacting a compound of formula (VII), wherein $R_3$, $R_4$, $R_5$, $R_6$, $R_7$ and $R_8$ are as defined above with a compound of formula $C_1$-$C_2$-alkyl-M or Ph-M, where Ph is an optionally substituted phenyl group and M is lithium or the radical-MgX, where X is halogen, preferably bromine, provided that an inverse addition is done and the temperature is kept low enough to avoid subsequent unwanted reactions.

A compound of formula (II) wherein $R_{12}$ is halogen, may be obtained from a compound of formula (II) wherein $R_{12}$ is hydroxy, by treatment with an appropriate halogenating agent, for example by treatment with $SOCl_2$ or $PBr_3$ at temperatures ranging from 0° to 60° C., preferably at room temperature.

Compounds of formula (III) are known or may be prepared by known methods, as reported in Chemical Comm. 1970, 850. The compounds with formula (IV) in which E is $(R_eO)_2$→(O)-($R_e$ as defined above) are prepared by reacting a compound of formula (VIII)

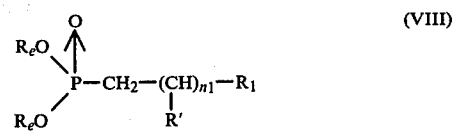

(VIII)

wherein
$R_e$, $n_1$ and $R_1$ are as defined above
and R' is hydrogen or amino,
with at least one molar equivalent of one of the following bases: an alkali metal or alkaline earth metal hydride like sodium, potassium, lithium or calcium hydride, an alkali metal or alkaline earth metal alkoxide, like sodium or potassium tert-butylate, an alkali metal or alkaline earth metal amide, like sodium amide, or an alkali metal or alkaline earth metal salt of a carboxamide, like N-sodiumacetamide and N-sodiumsuccinimide.

Compounds with formula (IV) in which E is $(C_6H_5)_3P$— are prepared by reacting a compound with formula (IX)

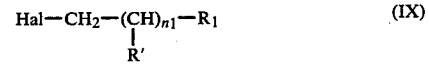

(IX)

wherein n₁, R' and R₁ are as defined above and Hal is halogen, with 1.1–1.3 molar equivalents of triphenylphosphine in an organic solvent like benzene, acetonitrile or diethyl ether and then treating the product phosphonium salt with an equivalent quantity of an inorganic base like NaOH, KOH, Na₂CO₃ or NaHCO₃.

A compound of formula (V) may be obtained by diazotizing a compound of formula (X)

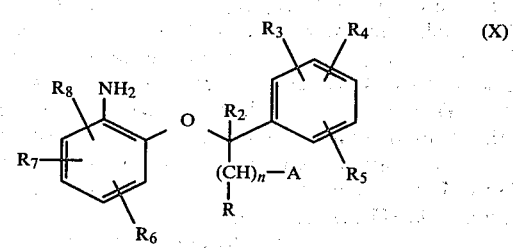

(X)

wherein
R, R₂, R₃, R₄, R₅, R₆, R₇, R₈, A and n are as defined above, by conventional manner, for example with NaNO₂ and HCl or H₂SO₄, at temperatures ranging from about 0° C. to about 10° C.

A compound of formula (VI) may be obtained by reacting a compound of formula (XI)

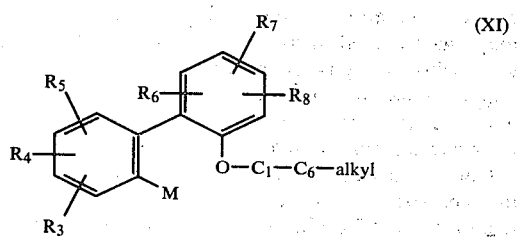

(XI)

wherein R₃, R₄, R₅, R₆, R₇, R₈ and M are as defined above, with a compound of formula (XII)

(XII)

wherein R'₂, n and R₁₃ are as defined above.

The reaction between a compound of formula (XI) and a compound of formula (XII) may be carried out by following known methods for this kind of reaction, for example, in aprotic solvents, e.g. tetrahydrofuran or toluene, and at temperatures from about −78° C. to the room temperature. Compounds of formula (VII) are known or may be prepared from known compounds by known methods.

Compounds of formula (VIII) are prepared using standard methods, for example those described by Corey et al. in J. Amer. Chem. Soc., 1968, 90, 3247 and 1966, 88, 5654. Compounds with formula (IX) are also prepared following standard procedures.

Compounds of formula (X), wherein A is R₁, wherein R₁ is as defined above, are known or may be obtained by known methods.

Compounds of formula (x) wherein A is a protected carboxy group, may be obtained by reacting a compound of formula (XIII)

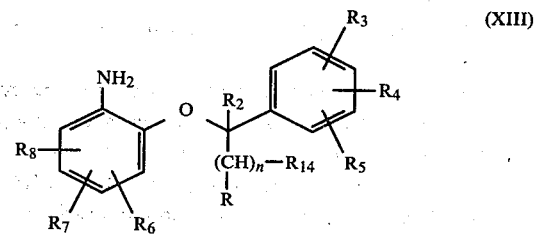

(XIII)

wherein R₁₄ is a carboxy group or a reactive derivative thereof, R₂, R₃, R₄, R₅, R₆, R₇, R₈, R and n are as defined above, with a suitable carboxy protecting agent. In particular a compound of formula (X) in which A is the group

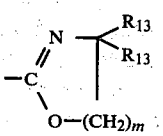

wherein m and R₁₃ are as defined above, may be obtained by reacting a compound of formula (XIII) with a suitable aminoalcohol, preferably 2-aminoethanol or 2-amino-2-methylpropanol, according to Can. J. Chem., 1970, 48, 983 and cyclizing the obtained amide, in the presence of SOCl₂ according to J. Org. Chem., 1975, 40, 1430.

Compounds of formula (XI) are known compounds or may be prepared according to known methods, for example as described in Chem. Ber., 1972, 105, 217. Also compounds of formula (XII) and (XIII) are known compounds as may be obtained through known methods from known compounds.

The compounds of the present invention are active on the gastrointestinal system, in particular they are endowed with anti-ulcerogenic, gastric anti-secretory and a very negligible anti-cholinergic activity and are therefore useful in therapy, for example in the prevention and treatment of peptic, e.g. duodenal, gastric and esophageal, ulcers and to inhibit gastric acid secretion.

The compounds of the invention are also useful for reducing the undesirable gastrointestinal side-effects resulting from systemic administration of anti-inflammatory prostaglandin synthetase inhibitors and may be, therefore, used for this purpose in association with them. The anti-ulcerogenic activity of the compounds of the invention is shown, e.g., by the fact that they are active in the test of the inhibition of restraint ulcers in rats, according to the method of Bonfils et al., (Thérapie, 1960, 5, 1096; Jap. J. Pharmac. 1945, 43, 5).

According to this method, the tested compounds were administered per os (p.o.) one hour before the immobilization. Six Sprague-Dawley male rats (100–120 g) fasted 24 hours were used for the experiment: a square flexible small-mesh wire netting was used for the immobilization and 4 hours after the immobilization the rats were sacrificed, their stomachs were removed and the lesions counted under a dissecting microscope.

Table 1 shows, for example, the approximate ED₅₀ value of the anti-ulcerogenic activity in the rat obtained for two of the compounds of the invention after oral administration:

TABLE 1

| Compound | Antiulcerogenic activity $ED_{50}$ p.o. |
|---|---|
| FCE 20524 | 4.8 mg/kg |
| FCE 20618 | 7.0 mg/kg |

As already stated above, the compounds of the invention own also gastric antisecretory activity, as shown e.g. by the fact that they proved to be active after intraduodenal administration in inhibiting the gastric secretion in rats according to the method of H. Shay et al. (Gastroenter., 1945, 43, 5).

According to this method the tested compounds were injected intraduodenally (i.d.) at the time of ligature.

Six Sprague-Dawley male rats (110–130 g) were used for each group. Twenty-four hours before the test, the rats were deprived of food but the water supply was maintained. On the day of the operation, the pylorus was ligated under light ether anaesthesia. Four hours after the ligature, the rats were sacrificed. The stomach secretion was collected and centrifugated at 3500 r.p.m. for 10 minutes and the volume, less sediment, was determined.

The amount of free hydrochloric acid in the gastric juice was determined by titration against 0.01N sodium hydroxide, to an end point of pH 7.

Table 2 shows, for example, the approximate $ED_{50}$ value of the antisecretory activity in the rat obtained for the compounds reported above in Table 1:

TABLE 2

| Compound | Antisecretory activity $ED_{50}$ i.d. |
|---|---|
| FCE 20524 | 6 mg/kg |
| FCE 20618 | 1.5 mg/kg |

Considering that many anti-ulcer agents display, as does atropine, a remarkable but undesired anti-cholinergic activity, the compounds of the invention were also assessed for their antagonism against syndrome induced by oxotremorine in mice, according to the method described by Leszkovszky G. P. and Tardos L. (Europ. J. Pharmac. 1971, 15, 310). According to this method 5 male mice, 20–25 g body weight, were used for each group.

Table 3 shows, for example, the approximate $ED_{50}$ value of the anti-cholinergic activity obtained according to the above method for the compounds reported in Table 1 and 2.

TABLE 3

| Compound | Anticholinergic activity $ED_{50}$ p.o. |
|---|---|
| FCE 20524 | >100 mg/kg |
| FCE 20618 | >100 mg/kg |

As anti-ulcerogenic and anti-secretory agents, the compounds of the invention are administered through usual routes, e.g. orally, parenterally or in the form of suppositories. Amount, from about 50 to about 200 mg pro dose, from 1 to 5 times daily for oral administration to adult humans are used. Compound FCE 20618 is, for example, preferably administered to adult humans orally at dosages from 100 to 150 mg pro dose, from 1 to 5 times daily.

The compounds of this invention possess also immunomodulating activity and in particular antiviral activity.

Their immunomodulating activity is, for example, proven by their capacity to modify the antibody response induced in mice by a suboptimal dose of sheep red blood cells (SRBC) injected by intraperitoneal route (i.p.).

Groups of ten female CD-1 mice were injected i.p. with $2 \times 10^6$ SRBC as antigen. The tested compounds were administered i.p. at two dosage levels: 50 and 5 mg/kg body weight, two hours before the administration of the antigen. A control group of mice received SRBC and saline instead of the compounds. Six days later the mice were killed and antibody titres against SRBC determined in their sera, according to Williams C. A.: Methods in Immunology and Immunochemistry, C. A. Williams and M. W. Chase, Eds. Academic Press, New York, Vol. II, page 152, 1977.

Augmentation of haemolytic antibody production was shown, for example, by compounds FCE 20696 and FCE 21849. These two compounds increased the antibody titers several fold as compared to control group.

The antiviral activity of the compound of the invention was, for example, evaluated on influenza and herpes simplex viruses experimental infections in mice.

Groups of CD-1 mice were infected intranasally with the strain APR 8 of influenza virus and other groups were infected intraperitoneally with the strain 1RC of herpes simplex virus. The tested compounds were administered through various routes, e.g. intraperitoneally, subcutaneously, orally.

The effect of the tested compounds, against the influenza virus, was evaluated on the basis of the number of lung lesions and, against the herpes infection, the parameter considered was the protection from mortality since, as is known, herpes simplex infection is lethal in mice. The tested compounds was found to be effective in protecting the mice from both the viral infections. For example compound FCE 20696, when administered in a single dose either one or two days after the infection, showed remarkable pharmacological activity by reducing substantially the number of lung lesions in the influenza infection and protecting up to 45% of animals from death in the herpes simplex infection.

The compounds of formula (I) are therefore useful in the therapy of transplant reactions, for example transplants of kidneys, heart, bone marrow, skin and endocrine glands. Other areas of pathology, in which the immunomodulating properties of these compounds are of therapeutic benefit: the therapy of neoplastic diseases, acute and chronic infections of both bacterial and viral origin, and of diseases characterized by an immunologic imbalance, like primary or acquired immunodeficiencies and autoimmune disorders. This last category includes rheumatoid arthritis, systemic lupus erythematosus, glomerulonephritis, vasculitis and blood dyscrasias. The therapeutic regimen for the different clinical syndromes must be adapted to the type of pathology.

In transplantation and infections diseases the time of onset and the clinical course are, as a rule, known; conversely, the onset of immunological disorders is unknown and their clinical course is generally long and complex. Hence the therapeutic dose must be determined for each single clinical case, taking into account also the fact that it depends also on the route of administration. The oral route is employed, in general, for all conditions requiring such compounds. Preference is given to the parenteral route, e.g. intravenous injection or infusion, for the prevention of rejection and the treatment of acute infections. In the latter case also topical applications may be used.

For maintenance regimens the oral or parenteral, e.g. intramuscular or subcutaneous, route is preferred. For these purposes the compounds of the invention, for example, compound FCE 20696, can be administered orally at doses ranging e.g. from about 5 to about 100 mg/kg of body weight per day; for example a total of from about 0.35 g to about 7.00 g of the active compound for a subject of 70 kg of body weight can be administered in a 24 hour period.

Doses of active compounds ranging e.g. from about 5 to about 100 mg/kg of body weight can be used also for the parenteral administration. Of course, these dosage regimens may be adjusted to provide the optimal therapeutic response.

The compounds of the invention are also endowed with an elevated lipid-lowering and anti-atherosclerotic activity. In particular they are active in lowering total serum cholesterol and triglycerides, in increasing the total serum HDL cholesterol.

As known, drugs selectively increasing the HDL-cholesterol concentration in blood and/or the ratio between $\alpha$ and $\beta$ lipoprotein cholesterol are useful in the prevention and therapy of atherosclerosis: Glueck C. J., Artery, 2:196 (1976); Day C. E. in Frank-H-Clarke (Ed.) Annual Reports in Medicinal Chemistry, 13:184, Chapter 20-Academic Press, N.Y. 1978.

The activity of the compounds of the invention was evaluated: (1) on groups of Icem:CER (SPF Caw) male rats, fed for six days with hypercholesterolaemic diet according to C. E. Day: Shur P. E., Shultz H. R., Day C. E. (Ed.) Atherosclerosis and drug discovery Plenum Pub. Corp., 217 (1976): Experiment 1; or (2) or groups of Iva-SIV (SPF) male rats fed standard MS/K Altromin ® diet: Experiment 2. MS/K Altromin is a trade mark.

The tested compounds were suspended in Methocel (methyl-cellulose, a 0.5% solution in water) and administered by stomach tube at the dose of 50 mg/kg for 4 days in both the experiments.

Groups of animals were treated with the suspending agent only (control groups).

The total serum cholesterol was determined with the method of Allain, Clin. Chem., 1974, 20, 470.

The serum triglycerides were determined with the method of Mendez, J. Clin. Chem., 1975, 21, 768.

The total serum HDL cholesterol was determined according to Demacker P. N. H., Clin. Chem., 1977, 23, 1238.

The total $\beta$-lipoprotein cholesterol was determined by difference between total serum cholesterol and HDL cholesterol. Statistical analysis in experiment 1 and 2 was performed by the Student's t test for independent samples or by the Cochran's test when the variances were not homogeneous at the F ratio test [Bliss C. I., Statistics in Biology, Vol. 1, page 213 McGraw Hill Book Company, New York 1967; Cochran W. G., Cox C. H., Experimental designs-J. Willey and Sons Inc., New York, II Ed. (1968), page 100].

Table 4 shows that, in the animals treated with hypercholesterolaemic diet (Experiment 1), the tested compounds, for example FCE 20881), were found to decrease the total serum cholesterol and to increase the total HDL cholesterol.

Table 5 shows that, in the animal fed standard MS/K Altromin diet (Experiment 2), the tested compounds (for example FCE 20881), were found to decrease the total serum cholesterol, in particular $\beta$-lipoprotein cholesterol and serum triglycerides.

TABLE 4

(Experiment No. 1)

| Treatment | Dose mg/kg/os | Animal number | Total serum cholesterol mg/100 ml mean ± S.E. | Student's t test result | Serum HDL total cholesterol mg/100 ml mean ± S.E. | Student's t test result |
|---|---|---|---|---|---|---|
| Control | * | 5 | 459.6 ± 51.7 | p = 3.94 HS | 13.2 ± 1.8 | p = 5.28 HS |
| FCE 20881 | 50 | 5 | 240.0 ± 20.7 | | 23.2 ± 0.5 | |

*Methocel (0.5% in distilled water): 5 ml/kg/os
HS = highly significant (p <0.07)

TABLE 5

(Experiment No. 2)

| Treatment | Dose mg/kg/os | Animal number | Total serum cholesterol mg/100 ml mean ± S.E. | Student's t test result | $\beta$-lipoprotein cholesterol mg/100 ml mean ± S.E. | Student's t test result | Serum trygylcerides mg/100 ml mean ± S.E. | Student's t test result |
|---|---|---|---|---|---|---|---|---|
| Control | * | 10 | 66.3 ± 1.7 | p = 3.84 HS | 27.1 ± 1.1 | p = 4.70 HS | 228.7 ± 18.9 | p = 2.61 S |
| FCE 20881 | 50 | 10 | 57.7 ± 1.5 | | 20.5 ± 0.8 | | 168.3 ± 13.4 | |

*Methocel (0.5% in distilled water): 5 ml/kg/os
S = significant (p <0.05)
HS = highly significant (p <0.01)

In view of their high lipid-lowering activity, these new compounds are used in the therapy of hyperlipidemia. They may be administered in a variety of dosage forms, e.g. orally in the form of tablets, capsules, sugar or film coated tablets, liquid solutions or suspensions; rectally, in the form of suppositories, parenterally, e.g. subcutaneously, intramuscularly or by intravenous injection or infusion.

The dosage of these compounds depends on the age, weight, conditions of the patient and administration route; for example, for the compound FCE 20881, the dosage adopted for oral administration in adult ranges from about 50 to about 200 mg pro dose, from 1 to 2 times daily, preferably from 100 to 200 mg pro dose once a day.

The toxicity of the compounds of the invention is negligible. Nine hours food deprived mice were treated orally with single administration of increasing doses, then housed and normally fed. The orientative acute toxicity ($LD_{50}$) was assessed on the seventh day after the treatment and, for example, the following data were obtained:

| | |
|---|---|
| FCE 20770: $LD_{50}$ | >400 <800 mg/kg |
| FCE 20493: $LD_{50}$ | >400 <800 mg/kg |
| FCE 20519: $LD_{50}$ | >800 mg/kg |
| FCE 20562: $LD_{50}$ | >400 <800 mg/kg |
| FCE 20518: $LD_{50}$ | >800 mg/kg |
| FCE 20561: $LD_{50}$ | >800 mg/kg |
| FCE 20881: $LD_{50}$ | >400 <800 mg/kg |
| FCE 20521: $LD_{50}$ | >800 mg/kg |
| FCE 20524: $LD_{50}$ | >400 <800 mg/kg |
| FCE 20618: $LD_{50}$ | >400 <800 mg/kg |
| FCE 20696: $LD_{50}$ | >400 <800 mg/kg |
| FCE 21849: $LD_{50}$ | >400 <800 mg/kg |

The above internal codes refer to the following compounds:
FCE 20770 = 6H,6-carboxy-6-methyl-2-chloro-dibenzo[b,d]pyran;
FCE 20493 = 6H,6-cyano-dibenzo[b,d]pyran;
FCE 20519 = 6H,6-cyano-6-methyl-dibenzo[b,d]pyran;
FCE 20562 = 6H,6-carboxy-6-methyl-dibenzo[b,d]pyran;
FCE 20518 = 6H,6-cyano-6-hydroxymethyl-dibenzo[b,d]pyran;
FCE 20561 = 6H,6-carboxy-6-hydroxymethyl-dibenzo[b,d]pyran;
FCE 20881 = 6H,6-carboxymethyl-dibenzo[b,d]pyran;
FCE 20521 = 6H,6-ethoxycarbonyl-dibenzo[b,d]pyran;
FCE 20524 = 6H,6-aminomethyl-dibenzo[b,d]pyran;
FCE 20618 = 6H,6-(1-piperazinyl)-dibenzo[b,d]pyran;
FCE 20696 = 6H,6-(2-dimethylaminoethoxycarbonyl)-dibenzo[b,d]pyran;
FCE 21849 = 6H,6-(2-diethylaminoethoxycarbonyl)-dibenzo[b,d]pyran.

The invention includes a pharmaceutical composition comprising a compound of the invention in association with a pharmaceutically acceptable excipient (which can be a carrier or diluent).

The pharmaceutical compositions of the invention are usually prepared following conventional methods and are administered in a pharmaceutically suitable form. For example, the solid oral forms may contain, together with the active compound, diluents, e.g., lactose, dextrose, saccharose, cellulose, corn starch and potato starch, lubricants e.g. silica, talc, stearic acid, magnesium or calcium stearate, and/or polyethylene glycols; binding agents, e.g. starches, arabic gums, gelatin, methylcellulose, carboxymethyl cellulose, polyvinyl pyrrolidone, disaggregating agents, e.g., a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactures in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, such as, sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin. Other pharmaceutical forms may be used for topical application, e.g. as creams, lotions or pastes for use in dermatological treatments. For these compositions the active ingredient may be mixed with conventional oleaginous or emulsifying excipients.

The following examples illustrate but do not limit the invention.

EXAMPLE 1

6H,6-hydroxy-dibenzo[b,d]pyran (10 g, 0.05 mol) was treated with $SOCl_2$ (50 ml) for 20 hours at room temperature. The thionyl chloride was evaporated, the organic residue was taken up with toluene and then the mixture was evaporated to dryness. The crude residue was taken up with anhydrous dimethylformamide (50 ml), then a saturated aqueous solution of KCN (0.05 mol) was added at 0° C. The temperature was allowed to rise to the room temperature and the mixture was maintained at this temperature for 20 hours. The reaction mixture was diluted with water and extracted with ethyl acetate. The organic phase was washed with water, dried over $Na_2SO_4$ and evaporated to dryness to give a clear oil which solidified. Crystallization from methyl alcohol gave 6H,6-cyano-dibenzo[b,d]pyran as white solid (4.2 g; 0.021 mol; yield 40%); m.p. 98°–100° C. By proceeding analogously the following compounds were obtained:

6H,6-cyano-6-methyl-dibenzo[b,d]pyran; m.p. 114°–116° C.
6H,6-cyano-6-ethyl-dibenzo[b,d]pyran;
6H,6-cyano-6-phenyl-dibenzo[b,d]pyran; m.p. 120°–123° C.
6H,6-cyano-1-methoxy-dibenzo[b,d]pyran;
6H,6-cyano-2-chloro-dibenzo[b,d]pyran; m.p. 128°–131° C.
6H,6-cyano-2-fluoro-dibenzo[b,d]pyran; m.p. 118°–121° C.
6H,6-cyano-2-nitro-dibenzo[b,d]pyran; m.p. 185°–196° C.
6H,6-cyano-2-methoxy-dibenzo[b,d]pyran; m.p. 122°–126° C.
6H,6-cyano-2-trifluoromethyl-dibenzo[b,d]pyran; m.p. 110°–113° C.
6H,6-cyano-8-chloro-dibenzo[b,d]pyran; m.p. 117°–120° C.
6H,6-cyano-8-fluoro-dibenzo[b,d]pyran; m.p. 113°–117° C.

6H,6-cyano-8-methoxy-dibenzo[b,d]pyran; m.p. 102°-105° C.

6H,6-cyano-1,10-dimethoxy-dibenzo[b,d]pyran; m.p. 102°-105° C.

6H,6-cyano-8,9,10-trimethoxy-dibenzo[b,d]pyran; m.p. 114°-115° C.

6H,6-cyano-6-methyl-1-methoxy-dibenzo[b,d]pyran;

6H,6-cyano-6-methyl-2-chloro-dibenzo[b,d]pyran; m.p. 111°-116° C.

6H,6-cyano-6-methyl-2-fluoro-dibenzo[b,d]pyran; m.p. 67°-71° C.

6H,6-cyano-6-methyl-2-nitro-dibenzo[b,d]pyran;

6H,6-cyano-6-methyl-2-methoxy-dibenzo[b,d]pyran; m.p. 94°-99° C.

6H,6-cyano-6-methyl-2-trifluoromethyl-dibenzo[b,d]pyran;

6H,6-cyano-6-methyl-8-chloro-dibenzo[b,d]pyran;

6H,6-cyano-6-methyl-8-fluoro-bidenzo[d,d]pyran;

6H,6-cyano-6-methyl-8-nitro-dibenzo[b,d]pyran;

6H,6-cyano-6-methyl-8-methoxy-dibenzo[b,d]pyran;

6H,6-cyano-6-methyl-1,10-dimethoxy-dibenzo[b,d]pyran, m.p. 115°-118° C.;

6H,6-cyano-6-methyl-8,9,10-trimethoxy-dibenzo[b,d]pyran, m.p. 108°-111° C.

EXAMPLE 2

6H,6-hydroxy-dibenzo[b,d]pyran (4 g; 0.02 mol) was dissolved in anhydrous benzene (50 ml). Trimethylsilylcyanide (1.98 g; 0.02 mol) and a catalytic amount of $ZnI_2$ were added to the solution, then the reaction mixture was stirred for 20 hours at room temperature. The solvent and excess of trimethylsilylcyanide were evaporated and the organic residue was taken up twice with toluene. The toluene was evaporated and the residue was separated by column chromatography using silica gel as support and chloroform as mobile phase to give 6H,6-cyano-dibenzo[b,d]pyran as white solid (2.5 g; 0.012 mol); m.p. 98°-100° C.

By proceeding analogously the following compounds were obtained:

6H,6-cyano-6-methyl-dibenzo[b,d]pyran; m.p. 114°-116° C.

6H,6-cyano-6-ethyl-dibenzo[b,d]pyran;

6H,6-cyano-6-phenyl-dibenzo[b,d]pyran: m.p. 120°-123° C.

6H,6-cyano-1-methoxy-dibenzo[b,d]pyran;

6H,6-cyano-2-chloro-dibenzo[b,d]pyran; m.p. 128°-131° C.

6H,6-cyano-2-fluoro-dibenzo[b,d]pyran; m.p. 118°-121° C.

6H,6-cyano-2-nitro-dibenzo[b,d]pyran; m.p. 185°-196° C.

6H,6-cyano-2-methoxy-dibenzo[b,d]pyran; m.p. 122°-126° C.

6H,6-cyano-2-trifluoromethyl-dibenzo[b,d]pyran; m.p. 110°-113° C.

6H,6-cyano-8-chloro-dibenzo[b,d]pyran; m.p. 117°-120° C.

6H,6-cyano-8-fluoro-dibenzo[b,d]pyran; m.p. 113°-117° C.

6H,6-cyano-8-methoxy-dibenzo[b,d]pyran; m.p. 102°-105° C.

6H,6-cyano-1,10-dimethoxy-dibenzo[b,d]pyran; m.p. 102°-105° C.

6H,6-cyano-8,9,10-trimethoxy-dibenzo[b,d]pyran; m.p. 114°-115° C.

6H,6-cyano-6-methyl-1-methoxy-dibenzo[b,d]pyran;

6H,6-cyano-6-methyl-2-chloro-dibenzo[b,d]pyran; m.p. 111°-116° C.

6H,6-cyano-6-methyl-2-fluoro-dibenzo[b,d]pyran; m.p. 67°-71° C.

6H,6-cyano-6-methyl-2-nitro-dibenzo[b,d]pyran;

6H,6-cyano-6-methyl-2-methoxy-dibenzo[b,d]pyran; m.p. 94°-99° C.

6H,6-cyano-6-methyl-2-trifluoromethyl-dibenzo[b,d]pyran;

6H,6-cyano-6-methyl-8-chloro-dibenzo[b,d]pyran;

6H,6-cyano-6-methyl-8-fluoro-dibenzo[b,d]pyran;

6H,6-cyano-6-methyl-8-nitro-dibenzo[b,d]pyran;

6H,6-cyano-6-methyl-8-methoxy-dibenzo[b,d]pyran;

6H,6-cyano-6-methyl-1,10-dimethoxy-dibenzo[b,d]pyran; m.p. 115°-118° C.;

6H,6-cyano-6-methyl-8,9,10-trimethoxy-dibenzo[b,d]pyran; m.p. 108°-111° C.

EXAMPLE 3

6H,6-hydroxy-dibenzo[b,d]pyran (4 g; 0.02 mol) was dissolved in anhydrous benzene and piperazine (35 g; 0.4 mol) dissolved 100 ml of anhydrous dimethylformamide was added all at once. The mixture was refluxed for 3 days and then poured in ice water. The organic layer was separated and the aqueous phase was extracted with ethyl acetate. The solvent was evaporated to dryness in vacuo and the residue was separated on a silica gel column (mobile phase $CHCl_3$:MEOH:32 % $NH_4OH$=190:10:1) to obtain 6H,6-(1-piperazinyl)-dibenzo[b,d]pyran as an oily substance which was converted into the hydrochloride in diethyl ether with the stoichiometric amount of 14% ethanolic solution of HCl (3 g; 50%); m.p. 240°-243° C.

Analogously the following compounds were obtained:

6H,6-[1-(4-methyl-piperazinyl)]-dibenzo[b,d]pyran; m.p. 118°-121° C.;

6H,6-[1-(4-phenyl-piperazinyl)]-dibenzo[b,d]pyran; m.p. 148°-150° C.;

6H,6-diisopropylamino-dibenzo[b,d]pyran;

6H,6-ditert.butylamino-dibenzo[b,d]pyran;

6H,6-(1-piperazinyl)-1-methoxy-dibenzo[b,d]pyran;

6H,6-(1-piperazinyl)-2-chloro-dibenzo[b,d]pyran; m.p. 178°-181° C.;

6H,6-(1-piperazinyl)-2-fluoro-dibenzo[b,d]pyran;

6H,6-(1-piperazinyl)-2-nitro-dibenzo[b,d]pyran;

6H,6-(1-piperazinyl)-2-methoxy-dibenzo[b,d]pyran;

6H,6-(1-piperazinyl)-2-trifluoromethyl-dibenzo[b,d]pyran;

6H,6-(1-piperazinyl)-8-chloro-dibenzo[b,d]pyran;

6H,6-(1-piperazinyl)-8-fluoro-dibenzo[b,d]pyran;

6H,6-(1-piperazinyl)-8-methoxy-dibenzo[b,d]pyran;

6H,6-(1-piperazinyl)-1,10-dimethoxy-dibenzo[b,d]pyran;

6H,6-(1-piperazinyl)-8,9,10-trimethoxy-dibenzo[b,d]pyran; m.p. 131°-134° C.;

6H,6-(1-piperazinyl)-6-methyl-1-methoxy-dibenzo[b,d]pyran;

6H,6-(1-piperazinyl)-6-methyl-2-chloro-dibenzo[b,d]pyran;

6H,6-(1-piperazinyl)-6-methyl-2-fluoro-dibenzo[b,d]pyran;

6H,6-(1-piperazinyl)-6-methyl-2-nitro-dibenzo[b,d]pyran;

6H,6-(1-piperazinyl)-6-methyl-2-methoxy-dibenzo[b,d]pyran;

6H,6-(1-piperazinyl)-6-methyl-2-trifluoromethyl-dibenzo[b,d]pyran;

6H,6-(1-piperazinyl)-6-methyl-8-chloro-dibenzo[b,d]pyran;
6H,6-(1-piperazinyl)-6-methyl-8-fluoro-dibenzo[b,d]pyran;
6H-6-(1-piperazinyl)-6-methyl-8-nitro-dibenzo[b,d]pyran;
6H,6-(1-piperazinyl)-6-methyl-8-methoxy-dibenzo[b,d]pyran;
6H,6-(1-piperazinyl)-6-methyl-1,10-dimethoxy-dibenzo[b,d]pyran;
6H,6-(1-piperazinyl)-6-methyl-8,9,10-trimethoxy-dibenzo[b,d]pyran;

EXAMPLE 4

Dibenzo[b,d]pyrilium perchlorate (28 g; 0.1 mol) was suspended in anhydrous benzene (200 ml); then KCN (1 mol) and a catalytic amount of a 18-crown-6-ether were added. The mixture was stirred for 2 days at room temperature. The solid was filtered and the solvent was evaporated to give an oil which solidified.

Crystallization from methyl alcohol gave 6H,6-cyano-dibenzo[b,d]pyran was white solid (10 g; yield 48%), m.p. 98°–100° C.

By proceeding analogously the following compounds were obtained:
6H,6-cyano-6-methyl-dibenzo[b,d]pyran; m.p. 114°–116° C.
6H,6-cyano-6-ethyl-dibenzo[b,d]pyran;
6H,6-cyano-6-phenyl-dibenzo[b,d]pyran; m.p. 120°–123° C.
6H,6-cyano-1-methoxy-dibenzo[b,d]pyran;
6H,6-cyano-2-chloro-dibenzo[b,d]pyran; m.p. 128°–131° C.
6H,6-cyano-2-fluoro-dibenzo[b,d]pyran; m.p. 118°–121° C.
6H,6-cyano-2-nitro-dibenzo[b,d]pyran; m.p. 185°–196° C.
6H,6-cyano-2-methoxy-dibenzo[b,d]pyran; m.p. 122°–126° C.
6H,6-cyano-2-trifluoromethyl-dibenzo[b,d]pyran; m.p. 110°–113° C.
6H,6-cyano-8-chloro-dibenzo[b,d]pyran; m.p. 117°–120° C.
6H,6-cyano-8-fluoro-dibenzo[b,d]pyran; m.p. 113°–117° C.
6H,6-cyano-8-methoxy-dibenzo[b,d]pyran; m.p. 102°–105° C.
6H,6-cyano-1,10-dimethoxy-dibenzo[b,d]pyran; m.p. 102°–105° C.
6H,6-cyano-8,9,10-trimethoxy-dibenzo[b,d]pyran; m.p. 114°–115° C.
6H,6-cyano-6-methyl-1-methoxy-dibenzo[b,d]pyran;
6H,6-cyano-6-methyl-2-chloro-dibenzo[b,d]pyran; m.p. 111°–116° C.
6H,6-cyano-6-methyl-2-fluoro-dibenzo[b,d]pyran; m.p. 67°–71° C.
6H,6-cyano-6-methyl-2-nitro-dibenzo[b,d]pyran;
6H,6-cyano-6-methyl-2-methoxy-dibenzo[b,d]pyran; m.p. 94°–99° C.
6H,6-cyano-6-methyl-2-trifluoromethyl-dibenzo[b,d]pyran;
6H,6-cyano-6-methyl-8-chloro-dibenzo[b,d]pyran;
6H,6-cyano-6-methyl-8-fluoro-dibenzo[b,d]pyran;
6H,6-cyano-6-methyl-8-nitro-dibenzo[b,d]pyran;
6H,6-cyano-6-methyl-8-methoxy-dibenzo[b,d]pyran;
6H,6-cyano-6-methyl-1,10-dimethoxy-dibenzo[b,d]pyran; m.p. 115°–118° C.;
6H,6-cyano-6-methyl-8,9,10-trimethoxy-dibenzo[b,d]pyran; m.p. 108°–111° C.

EXAMPLE 5

A solution of 6H,6-hydroxy-dibenzo[b,d]pyran (7.2 g; 0.036 mol) and (19.3 g; 0.054 mol) of the ylid from ethoxycarbonylmethyl-triphenyl-phosphonium bromide in 200 ml of benzene was refluxed for 3 days. The solvent was evaporated under reduced pressure and the residue taken up with diethyl ether. The solid was filtered out and the ether evaporated to dryness. The residue was separated on a silica-gel column (mobile phase $CHCl_3:C_2H_5OH=300:10$) to give 7 g (72%) of 6H,6-ethoxycarbonylmethyl-dibenzo[b,d]pyran; m.p. 45°–47° C.

By proceeding analogously the following compounds were obtained:
6H,6-ethoxycarbonylmethyl-6-methyl-dibenzo[b,d]pyran; m.p. 56°–59° C.;
6H,6-ethoxycarbonylmethyl-6-ethyl-dibenzo[b,d]pyran;
6H,6-ethoxycarbonylmethyl-6-phenyl-dibenzo[b,d]pyran; m.p. 71°–73° C.;
6H,6-ethoxycarbonylmethyl-1-methoxy-dibenzo[b,d]pyran;
6H,6-ethoxycarbonylmethyl-2-chloro-dibenzo[b,d]pyran; m.p. 61°–64° C.;
6H,6-ethoxycarbonylmethyl-2-fluoro-dibenzo[b,d]pyran; m.p. 49°–52° C.;
6H,6-ethoxycarbonylmethyl-2-nitro-dibenzo[b,d]pyran; m.p. 75°–78° C.;
6H,6-ethoxycarbonylmethyl-2-methoxy-dibenzo[b,d]pyran; m.p. 39°–42° C.;
6H,6-ethoxycarbonylmethyl-2-trifluoromethyl-dibenzo[b,d]pyran
6H,6-ethoxycarbonylmethyl-8-chloro-dibenzo[b,d]pyran;
6H,6-ethoxycarbonylmethyl-8-fluoro-dibenzo[b,d]pyran;
6H,6-ethoxycarbonylmethyl-8-methoxy-dibenzo[b,d]pyran;
6H,6-ethoxycarbonylmethyl-1,10-dimethoxy-dibenzo[b,d]pyran; m.p. 44°–47° C.;
6H,6-ethoxycarbonylmethyl-8,9,10-trimethoxy-dibenzo[b,d]pyran; m.p. 58°–61° C.;
6H,6-ethoxycarbonylmethyl-6-methyl-1-methoxy-dibenzo[b,d]pyran;
6H,6-ethoxycarbonylmethyl-6-methyl-2-chloro-dibenzo[b,d]pyran; m.p. 67°–70° C.;
6H,6-ethoxycarbonylmethyl-6-methyl-2-fluoro-dibenzo[b,d]pyran; m.p. 56°–59° C.;
6H,6-ethoxycarbonylmethyl-6-methyl-2-nitro-dibenzo[b,d]pyran; m.p. 71°–74° C.;
6H,6-ethoxycarbonylmethyl-6-methyl-2-methoxy-dibenzo[b,d]pyran; m.p. 53°–57° C.;
6H,6-ethoxycarbonylmethyl-6-methyl-2-trifluoromethyl-dibenzo[b,d]pyran;
6H,6-ethoxycarbonylmethyl-6-methyl-8-chloro-dibenzo[b,d]pyran;
6H,6-ethoxycarbonylmethyl-6-methyl-8-fluoro-dibenzo[b,d]pyran;
6H,6-ethoxycarbonylmethyl-6-methyl-8-nitro-dibenzo[b,d]pyran;
6H,6-ethoxycarbonylmethyl-6-methyl-8-methoxy-dibenzo[b,d]pyran;
6H,6-ethoxycarbonylmethyl-6-methyl-1,10-dimethoxy-dibenzo[b,d]pyran; m.p. 49°–52° C.;

6H,6-ethoxycarbonylmethyl-6-methyl-8,9,10-trimethoxy-dibenzo[b,d]pyran; m.p. 54°–57° C.

EXAMPLE 6

4,5 g (0.02 mol) of α-(2-amino-phenoxy)-phenylacetonitrile were dissolved in distilled water (60 ml). $H_2SO_4$ (18 ml; 0.08 mol) was added to the above solution at 0° C. and then $NaNO_2$ (1.7 g; 0.025 mol) dissolved in distilled water was added drop by drop. The unreacted excess of $NaNO_2$ was destroyed by adding a suitable amount of urea. $Cu(NO_3)_2.3H_2O$ (75 g; 0.31 mol) dissolved in distilled water (250 ml) and $Cu_2O$ (2.6 g; 0.018 mol) were added to the mixture under vigorous stirring and by keeping the temperature at 0° C. The crude obtained products was extracted with ethyl acetate, washed with water, dried on anhydrous $Na_2SO_4$, decolarated and finally evaporated to dryness. The residue taken up with pentene:isopropyl ether=9:1 gave 6H,6-cyano-dibenzo[b,d]pyran as a clear brown solid (2.5 g; yield 60%; m.p. 98°–100° C.).

Analogously, the following compounds were obtained:
6H,6-cyano-1-methoxy-dibenzo[b,d]pyran;
6H,6-cyano-2-chloro-dibenzo[b,d]pyran; m.p. 128°–131° C.
6H,6-cyano-2-fluoro-dibenzo[b,d]pyran; m.p. 118°–121° C.
6H,6-cyano-2-nitro-dibenzo[b,d]pyran; m.p. 185°–196° C.
6H,6-cyano-2-methoxy-dibenzo[b,d]pyran; m.p. 122°–126° C.
6H,6-cyano-2-trifluoromethyl-dibenzo[b,d]pyran; m.p. 110°–113° C.
6H,6-cyano-8-chloro-dibenzo[b,d]pyran; m.p. 117°–120° C.
6H,6-cyano-8-fluoro-dibenzo[b,d]pyran; m.p. 113°–117° C.
6H,6-cyano-8-methoxy-dibenzo[b,d]pyran; m.p. 102°–105° C.
6H,6-cyano-1,10-dimethoxy-dibenzo[b,d]pyran; m.p. 102°–105° C.
6H,6-cyano-8,9,10-trimethoxy-dibenzo[b,d]pyran; m.p. 114°–115° C.
6H,6-ethoxycarbonyl-dibenzo[b,d]pyran; m.p. 43°–45° C.;
6H,6-ethoxycarbonyl-1-methoxy-dibenzo[b,d]pyran;
6H,6-ethoxycarbonyl-2-chloro-dibenzo[b,d]pyran; m.p. 49°–52° C.;
6H,6-ethoxycarbonyl-2-fluoro-dibenzo[b,d]pyran;
6H,6-ethoxycarbonyl-2-nitro-dibenzo[b,d]pyran;
6H,6-ethoxycarbonyl-2-methoxy-dibenzo[b,d]pyran; m.p. 39°–42° C.;
6H,6-ethoxycarbonyl-2-trifluoromethyl-dibenzo[b,d]pyran;
6H,6-ethoxycarbonyl-8-chloro-dibenzo[b,d]pyran;
6H,6-ethoxycarbonyl-8-fluoro-dibenzo[b,d]pyran;
6H,6-ethoxycarbonyl-8-methoxy-dibenzo[b,d]pyran;
6H,6-ethoxycarbonyl-1,10-dimethoxy-dibenzo[b,d]pyran;
6H,6-ethoxycarbonyl-8,9,10-trimethoxy-dibenzo[b,d]pyran; m.p. 61°–63° C.;
6H,6-[2-(4',4'-dimethyl-oxazolinyl)]-dibenzo[b,d]pyran.

EXAMPLE 7

A solution of α-(4-pyridyl)-2-(2-methoxy-phenyl)-benzyl alcohol (17.7 g; 0.061 mol) in 120 ml of 48% HBr was refluxed for 3 hours. On cooling, yellow crystals of 6H,6-(4-pyridyl)-dibenzo[b,d]pyran hydrobromide separated, which was washed with icy water (11.2 g; yield 70%); m.p. 240° C. (dec.).

By proceeding analogously the following compounds were obtained:
6H,6-(3-pyridyl)-dibenzo[b,d]pyran;.HBr m.p. 207°–211° C.;
6H,6-(2-pyridyl)-dibenzo[b,d]pyran;.HCl m.p. 153°–157° C.;
6H,6-(2-pyrazinyl)-dibenzo[b,d]pyran.

EXAMPLE 8

6H,6-(4,4-dimethyl)-oxazolin-2-yl-dibenzo[b,d]pyran (4.2 g; 0.015 mol) dispersed in 3N HCl (100 ml) was refluxed for 10 min. The solvent was evaporated to dryness and the residue, taken up with a 20% solution of NaOH in $CH_3OH/H_2O$ (1/1) (100 ml), was refluxed for 30 min. Methyl alcohol was evaporated and the residue, taken up with water, was acidified. The solid product was filtrated and washed with water, then dried under vacuum in oil-bath for 24 hours, thus giving 6H,6-carboxy-dibenzo[b,d]pyran (3.2 g; yield 95%); m.p. 184°–186° C.

EXAMPLE 9

6H,6-(4,4-dimethyl)-oxazolin-2-yl-dibenzo[b,d]pyran (4.2 g; 0.015 mol) was dissolved into 7% ethanolic sulphuric acid (120 ml) and refluxed for 15 hours. The solvent was evaporated off and the residue, taken up with diethyl ether, was washed with 10% $NaHCO_3$ solution and then with water. The solvent was evaporated, the residue decoloured and the residual solvent evaporated off, thus giving 6H,6-ethoxycarbonyl-dibenzo[b,d]pyran as an orange oil which solidifies by treatment with pentane under cooling. (3.4 g; yield 90%); m.p. 44°–46° C.

EXAMPLE 10

6H,6-cyano-6-methyl-2-chloro-dibenzo[b,d]pyran (6.3 g; 0.025 mol) and NaOH (6.3 g; 0.16 mol) were dissolved in 80% $C_2H_5OH$ (100 ml) and the solution refluxed for 16 hours. After evaporation of the solvent the residue was dissolved in water and the solution washed with diethyl ether. The aqueous solution was then acidified with 23% HCl and extracted with ethyl acetate. The 6H,6-carboxy-6-methyl-2-chloro-dibenzo[b,d]pyran was obtained by evaporating the solution to dryness; (5.4 g; 80%); m.p. 174°–177° C.

By proceeding analogously the following compounds were obtained:
6H,6-carboxy-dibenzo[b,d]pyran; m.p. 184°–186° C.;
6H,6-carboxy-6-methyl-dibenzo[b,d]pyran; m.p. 147°–151° C.;
6H,6-carboxy-6-hydroxymethyl-dibenzo[b,d]pyran; m.p. 180°–182° C.;
6H,6-carboxy-6-ethyl-dibenzo[b,d]pyran; m.p. 157°–158° C.;
6H,6-carboxy-6-phenyl-dibenzo[b,d]pyran; m.p. 161°–163° C.;
6H,6-carboxy-1-methoxy-dibenzo[b,d]pyran;
6H,6-carboxy-2-chloro-dibenzo[b,d]pyran; m.p. 164°–167° C.;
6H,6-carboxy-2-fluoro-dibenzo[b,d]pyran; m.p. 148°–152° C.;
6H,6-carboxy-2-nitro-dibenzo[b,d]pyran; m.p. 196°–199° C.;
6H,6-carboxy-2-methoxy-dibenzo[b,d]pyran; m.p. 137°–140° C.;
6H,6-carboxy-2-trifluoromethyl-dibenzo[b,d]pyran;

6H,6-carboxy-8-chloro-dibenzo[b,d]pyran;
6H,6-carboxy-8-fluoro-dibenzo[b,d]pyran;
6H,6-carboxy-8-methoxy-dibenzo[b,d]pyran;
6H,6-carboxy-1,10-dimethoxy-dibenzo[b,d]pyran;
6H,6-carboxy-8,9,10-trimethoxy-dibenzo[b,d]pyran; m.p. 135°–138° C.;
6H,6-carboxy-6-methyl-1-methoxy-dibenzo[b,d]pyran;
6H,6-carboxy-6-methyl-2-fluoro-dibenzo[b,d]pyran; m.p. 142°–145° C.;
6H,6-carboxy-6-methyl-2-nitro-dibenzo[b,d]pyran; m.p. 187°–190° C.;
6H,6-carboxy-6-methyl-2-methoxy-dibenzo[b,d]pyran; m.p. 133°–136° C.;
6H,6-carboxy-6-methyl-2-trifluoromethyl-dibenzo[b,d]pyran;
6H,6-carboxy-6-methyl-8-chloro-dibenzo[b,d]pyran;
6H,6-carboxy-6-methyl-8-fluoro-dibenzo[b,d]pyran;
6H,6-carboxy-6-methyl-8-nitro-dibenzo[b,d]pyran;
6H,6-carboxy-6-methyl-8-methoxy-dibenzo[b,d]pyran;
6H,6-carboxy-6-methyl-1,10-dimethoxy-dibenzo[b,d]pyran; m.p. 139°–142° C.;
6H,6-carboxy-6-methyl-8,9,10-trimethoxy-dibenzo[b,d]pyran., m.p. 149°–152° C.
6H,6-(carboxy-aminomethyl)-dibenzo[b,d]pyran; m.p. 128°–145° C.
6H,6-(carboxy-aminomethyl)-6-methyl-dibenzo[b,d]pyran;
6H,6-(carboxy-aminomethyl)-1-methoxy-dibenzo[b,d]pyran;
6H,6-(carboxy-aminomethyl)-2-chloro-dibenzo[b,d]pyran;
6H,6-(carboxy-aminomethyl)-8-chloro-dibenzo[b,d]pyran; m.p. 137°–152° C.;
6H,6-(carboxy-aminomethyl)-8-fluoro-dibenzo[b,d]pyran;
6H,6-(carboxy-aminomethyl)-8,9,10-trimethoxy-dibenzo[b,d]pyran.

EXAMPLE 11

A solution of 6H,6-(cyano-hydroxy-methyl)-dibenzo[b,d]pyran (24 g; 0.1 mol) in 100 ml of dioxane and 200 ml of 37% HCl was refluxed for 3 days. The dioxane was distilled off; the solution was made basic through 35% NaOH and washed twice with diethyl ether. After acidification with 8% HCl, the precipitate was extracted with ethyl acetate. The obtained organic solution was washed thoroughly with water, treated with charcoal, dried on sodium sulfate and evaporated to dryness.

The residue was ground with a mixture of diisopropyl ether: pentene=1:1 to obtain 6H,6-(carboxy-hydroxy-methyl)-dibenzo[b,d]pyran (16.4 g; yield 64%) as a mixture of diasteroisomers approximately in the 1:1 ratio; m.p. 137°–147° C.

By proceeding analogously the following compounds were obtained:
6H,6-(carboxy-hydroxy-methyl)-6-methyl-dibenzo[b,d]pyran; m.p. 134°–147° C.;
6H,6-(carboxy-hydroxy-methyl)-1-methoxy-dibenzo[b,d]pyran; m.p. 116°–130° C.;
6H,6-(carboxy-hydroxy-methyl)-2-chloro-dibenzo[b,d]pyran;
6H,6-(carboxy-hydroxy-methyl)-2-fluoro-dibenzo[b,d]pyran; m.p. 119°–135° C.;
6H,6-(carboxy-hydroxy-methyl)-2-nitro-dibenzo[b,d]pyran;
6H,6-(carboxy-hydroxy-methyl)-2-methoxy-dibenzo[b,d]pyran; m.p. 120°–140° C.;
6H,6-(carboxy-hydroxy-methyl)-2-trifluoromethyl-dibenzo[b,d]pyran; m.p. 97°–123°
6H,6-(carboxy-hydroxy-methyl)-8-chloro-dibenzo[b,d]pyran;
6H,6-(carboxy-hydroxy-methyl)-8-fluoro-dibenzo[b,d]pyran;
6H,6-(carboxy-hydroxy-methyl)-8-nitro-dibenzo[b,d]pyran;
6H,6-(carboxy-hydroxy-methyl)-8-methoxy-dibenzo[b,d]pyran;
6H,6-(carboxy-hydroxy-methyl)-1,10-dimethoxy-dibenzo[b,d]pyran; m.p. 126°–137° C.;
6H,6-(carboxy-hydroxy-methyl)-8,9,10-trimethoxy-dibenzo[b,d]pyran, m.p. 131°–147° C.

EXAMPLE 12

6H,6-carboxy-6-methyl-2-chlorodibenzo[b,d]pyran (4.1 g; 0.015 mol) was dissolved in 100 ml of absolute ethanol and the solution was refluxed for 16 hours while gaseous HCl was bubbled in. The solvent was evaporated to dryness, the residue was redissolved in diethyl ether and the organic solution washed with N/10 NaOH and with water to neutrality. The 6H,6-ethoxycarbonyl-6-methyl-2-chlorodibenzo[b,d]pyran was obtained as a thick oil after evaporation of the ether and was solidified with pentane to give 4.3 g (95%) of product as white crystals; m.p. 62°–65° C.

By proceeding analogously the following compounds were obtained:
6H,6-ethoxycarbonyl-dibenzo[b,d]pyran; m.p. 43°–45° C.;
6H,6-ethoxycarbonylmethyl-dibenzo[b,d]pyran; m.p. 45°–47° C.;
6H,6-(2-ethoxycarbonylethyl)-dibenzo[b,d]pyran; m.p. 29°–32° C.;
6H,6-(3-ethoxycarbonylpropyl)-dibenzo[b,d]pyran;
6H,6-ethoxycarbonyl-6-methyl-dibenzo[b,d]pyran; N.M.R. (CCl$_4$)δ 1.03 (t,3H,CH$_2$CH$_3$); 1.9 (s,3H,CH$_3$); 3.95 (q,2H,CH$_2$); 6.75–7.7 (m,8H);
6H,6-ethoxycarbonylmethyl-6-methyl-dibenzo[b,d]pyran; m.p. 56°–59° C.;
6H,6-ethoxycarbonylmethyl-6-hydroxymethyl-dibenzo[b,d]pyran;
6H,6-(2-ethoxycarbonylethyl)-6-methyl-dibenzo[b,d]pyran;
6H,6-(3-ethoxycarbonylpropyl)-6-methyl-dibenzo[b,d]pyran;
6H,6-(2-dimethylaminoethyl-carbonyl)-dibenzo[b,d]pyran; .HCl m.p. 158°–160° C.;
6H,6-(2-dimethylaminoethoxy-carbonyl)-6-methyl-dibenzo[b,d]pyran; .HCl m.p. 165°–167° C.;
6H,6-(2-dimethylaminoethoxy-carbonyl)-6-ethyl-dibenzo[b,d]pyran; .HCl, m.p. 147°–150° C.;
6H,6-(2-dimethylaminoethoxy-carbonyl)-6-propyl-dibenzo[b,d]pyran;
6H,6-(2-dimethylaminoethoxy-carbonyl)-1-methoxy-dibenzo[b,d]pyran; .HCl, m.p. 139°–142° C.;
6H,6-(2-dimethylaminoethoxy-carbonyl)-2-chloro-dibenzo[b,d]pyran; .HCl, m.p. 183°–186° C.;
6H,6-(2-dimethylaminoethoxy-carbonyl)-2-fluoro-dibenzo[b,d]pyran; .HCl, m.p. 163°–166° C.;
6H,6-(2-dimethylaminoethoxy-carbonyl)-2-nitro-dibenzo[b,d]pyran; .HCl, m.p. 187°–190° C.;
6H,6-(2-dimethylaminoethoxy-carbonyl)-2-methoxy-dibenzo[b,d]pyran; .HCl, m.p. 146°–149° C.;
6H,6-(2-dimethylaminoethoxy-carbonyl)-2-trifluoromethyl-dibenzo[b,d]pyran;

6H,6-(2-dimethylaminoethoxy-carbonyl)-8-chloro-dibenzo[b,d]pyran; .HCl, m.p. 174°-177° C.;
6H,6-(2-dimethylaminoethoxy-carbonyl)-8-fluoro-dibenzo[b,d]pyran;
6H,6-(2-dimethylaminoethoxy-carbonyl)-8-nitro-dibenzo[b,d]pyran; .HCl, m.p. 178°-181° C.;
6H,6-(2-dimethylaminoethoxy-carbonyl)-8-methoxy-dibenzo[b,d]pyran;
6H,6-(2-dimethylaminoethoxy-carbonyl)-1,10-dimethoxy-dibenzo[b,d]pyran; .HCl, m.p. 147°-150° C.;
6H,6-(2-diethylaminoethoxy-carbonyl)-dibenzo[b,d]pyran; oil $n_D^{25} = 1.5841$;
6H,6-(2-dimethylaminoethoxy-carbonyl)-8,9,10-trimethoxy-dibenzo[b,d]pyran; .HCl, m.p. 162°-165° C.;
6H,6-(2-dimethylaminoethoxy-carbonylmethyl)-dibenzo[b,d]pyran; .HCl, m.p. 136°-139° C.;
6H,6-(2-dimethylaminoethoxy-carbonylethyl)-dibenzo[b,d]pyran;
6H,6-ethoxycarbonyl-1-methoxy-dibenzo[b,d]pyran;
6H,6-ethoxycarbonyl-2-chloro-dibenzo[b,d]pyran; m.p. 49°-52° C.;
6H,6-ethoxycarbonyl-2-fluoro-dibenzo[b,d]pyran; m.p. 43°-46° C.;
6H,6-ethoxycarbonyl-2-nitro-dibenzo[b,d]pyran;
6H,6-ethoxycarbonyl-2-methoxy-dibenzo[b,d]pyran; m.p. 39°-42° C.;
6H,6-ethoxycarbonyl-2-trifluoromethyl-dibenzo[b,d]pyran;
6H,6-ethoxycarbonyl-8-chloro-dibenzo[b,d]pyran;
6H,6-ethoxycarbonyl-8-fluoro-dibenzo[b,d]pyran;
6H,6-ethoxycarbonyl-8-nitro-dibenzo[b,d]pyran;
6H,6-ethoxycarbonyl-8-methoxy-dibenzo[b,d]pyran;
6H,6-ethoxycarbonyl-1,10-dimethoxy-dibenzo[b,d]pyran;
6H,6-ethoxycarbonyl-8,9,10-trimethoxy-dibenzo[b,d]pyran; m.p. 61°-63° C.;
6H,6-ethoxycarbonyl-methyl-1-methoxy-dibenzo[b,d]pyran;
6H,6-ethoxycarbonyl-methyl-2-chloro-dibenzo[b,d]pyran; m.p. 61°-64° C.;
6H,6-ethoxycarbonyl-methyl-2-fluoro-dibenzo[b,d]pyran; m.p. 49°-52° C.;
6H,6-ethoxycarbonyl-methyl-2-nitro-dibenzo[b,d]pyran; m.p. 75°14 78° C.;
6H,6-ethoxycarbonyl-methyl-2-methoxy-dibenzo[b,d]pyran; m.p. 39°-42° C.;
6H,6-ethoxycarbonyl-methyl-2-trifluoromethyl-dibenzo[b,d]pyran;
6H,6-ethoxycarbonyl-methyl-8-chloro-dibenzo[b,d]pyran;
6H,6-ethoxycarbonyl-methyl-8-fluoro-dibenzo[b,d]pyran;
6H,6-ethoxycarbonyl-methyl-8-nitro-dibenzo[b,d]pyran;
6H,6-ethoxycarbonyl-methyl-8-methoxy-dibenzo[b,d]pyran;
6H,6-ethoxycarbonyl-methyl-1,10-dimethoxy-dibenzo[b,d]pyran; m.p. 44°-47° C.;
6H,6-ethoxycarbonyl-methyl-8,9,10-trimethoxy-dibenzo[b,d]pyran; m.p. 58°-61° C.;
6H,6-(2-ethoxycarbonyl-ethyl)-1-methoxy-dibenzo[b,d]pyran;
6H,6-(2-ethoxycarbonyl-ethyl)-2-chloro-dibenzo[b,d]pyran; m.p. 63°-66° C.;
6H,6-(2-ethoxycarbonyl-ethyl)-2-fluoro-dibenzo[b,d]pyran; m.p. 48°-52° C.;
6H,6-(2-ethoxycarbonyl-ethyl)-2-nitro-dibenzo[b,d]pyran;
6H,6-(2-ethoxycarbonyl-ethyl)-2-methoxy-dibenzo[b,d]pyran;
6H,6-(2-ethoxycarbonyl-ethyl)-2-trifluoromethyl-dibenzo[b,d]pyran;
6H,6-(2-ethoxycarbonyl-ethyl)-8-chloro-dibenzo[b,d]pyran;
6H,6-(2-ethoxycarbonyl-ethyl)-8-fluoro-dibenzo[b,d]pyran;
6H,6-(2-ethoxycarbonyl-ethyl)-8-nitro-dibenzo[b,d]pyran;
6H,6-(2-ethoxycarbonyl-ethyl)-8-methoxy-dibenzo[b,d]pyran;
6H,6-(2-ethoxycarbonyl-ethyl)-1,10-dimethoxy-dibenzo[b,d]pyran;
6H,6-(2-ethoxycarbonyl-ethyl)-8,9,10-trimethoxy-dibenzo[b,d]pyran; m.p. 62°-65° C.;
6H,6-(ethoxycarbonyl-hydroxy-methyl)-dibenzo[b,d]pyran,
  N.M.R. CCl$_4$: δ 1 (t,3H,CH$_3$), 2.77 (bs,1H,OH), 3.95 (q,2H,CH$_2$) 6.65-7.7 (m,8H);
6H,6-(ethoxycarbonyl-hydroxy-methyl)-6-methyl-dibenzo[b,d]pyran;
6H,6-(ethoxycarbonyl-hydroxy-methyl)-2-chloro-dibenzo[b,d]pyran;
6H,6-(ethoxycarbonyl-hydroxy-methyl)-2-nitro-dibenzo[b,d]pyran;
6H,6-(ethoxycarbonyl-hydroxy-methyl)-2-methoxy-dibenzo[b,d]pyran;
6H,6-(ethoxycarbonyl-hydroxy-methyl)-2-hydroxy-dibenzo[b,d]pyran;
6H,6-(ethoxycarbonyl-hydroxy-methyl)-8,9,10-trimethoxy-dibenzo[b,d]pyran;

EXAMPLE 13

6H,6-carboxy-dibenzo[b,d]pyran (4 g; 0.018 mol) was suspended in thionyl chloride (40 ml; 0.55 mol) and kept at room temperature for 24 hours. The clear solution was taken up with toluene and the solvent was evaporated to dryness in vacuo. The crude residue was dissolved in 100 ml of diethyl ether and the obtained solution was added dropwise, at room temperature, to a solution of 2-dimethylamino-ethanol (53 ml; 0.053 mol) in 100 ml of diethyl ether. After half an hour the solution was washed with water and made anhydrous with sodium sulfate. The obtained 6H,6-(2-dimethylaminoethoxy-carbonyl)-dibenzo[b,d]pyran was precipitated as hydrochloride with 14% HCl alcoholic solution; (4.4 g; yield 75%); m.p. 158°-160° C.

By proceeding analogously the following compounds were obtained:
6H,6-ethoxycarbonyl-6-methyl-2-chloro-dibenzo[b,d]pyran; m.p. 62°-65° C.;
6H,6-ethoxycarbonyl-dibenzo[b,d]pyran; m.p. 43°-45° C.;
6H,6-ethoxycarbonylmethyl-dibenzo[b,d]pyran; m.p. 45°-47° C.;
6H,6-(2-ethoxycarbonylethyl)-dibenzo[b,d]pyran; m.p. 29°-32° C.;
6H,6-(3-ethoxycarbonylpropyl)-dibenzo[b,d]pyran;
6H,6-ethoxycarbonyl-6-methyl-dibenzo[b,d]pyran;
  N.M.R. (CCl$_4$) δ 1.03 (t, 3H,CH$_2$CH$_3$); 1.9 (s,3H,CH$_3$); 3.95 (q, 2H,CH$_2$); 6.75-7.7 (m,8H)
6H,6-ethoxycarbonylmethyl-6-methyl-dibenzo[b,d]pyran; m.p. 56°-59° C.;
6H,6-ethoxycarbonylmethyl-6-hydroxymethyl-dibenzo[b,d]pyran;
6H,6-(2-ethoxycarbonylethyl)-6-methyl-dibenzo[b,d]pyran;

6H,6-(3-ethoxycarbonylpropyl)-6-methyl-dibenzo[b,d]pyran;
6H,6-(2-dimethylaminoethoxy-carbonyl)-6-methyl-dibenzo[b,d]pyran, .HCl, m.p. 165°-167° C.;
6H,6-(2-dimethylaminoethoxy-carbonyl)-6-ethyl-dibenzo[b,d]pyran; .HCl, m;p. 147°-150° C.;
6H,6-(2-dimethylaminoethoxy-carbonyl)-6-propyl-dibenzo[b,d]pyran;
6H,6-(2-dimethylaminoethoxy-carbonyl)-1-methoxy-dibenzo[b,d]pyran; .HCl, m.p. 139°-142° C.;
6H,6-(2-dimethylaminoethoxy-carbonyl)-2-chloro-dibenzo[b,d]pyran; .HCl, m.p. 183°-186° C.;
6H,6-(2-dimethylaminoethoxy-carbonyl)-2-fluoro-dibenzo[b,d]pyran; .HCl, m.p. 163°-166° C.;
6H,6-(2-dimethylaminoethoxy-carbonyl)-2-nitro-dibenzo[b,d]pyran; .HCl, m.p. 187°-189° C.;
6H,6-(2-dimethylaminoethoxy-carbonyl)-2-methoxy-dibenzo[b,d]pyran; .HCl, m.p. 146°-149° C.;
6H,6-(2-dimethylaminoethoxy-carbonyl)-2-trifluoromethyl-dibenzo[b,d]pyran;
6H,6-(2-dimethylaminoethoxy-carbonyl)-8-chloro-dibenzo[b,d]pyran; .HCl, m.p. 174°-177° C.;
6H,6-(2-dimethylaminoethoxy-carbonyl)-8-fluoro-dibenzo[b,d]pyran;
6H,6-(2-dimethylaminoethoxy-carbonyl)-8-nitro-dibenzo[b,d]pyran; .HCl, m.p. 178°-181° C.;
6H,6-(2-dimethylaminoethoxy-carbonyl)-8-methoxy-dibenzo[b,d]pyran;
6H,6-(2-dimethylaminoethoxy-carbonyl)-1,10-dimethoxy-dibenzo[b,d]pyran; .HCl, m.p. 147°-150° C.;
6H,6-(2-diethylaminoethoxy-carbonyl)-dibenzo[b,d]pyran; oil $n_D^{25} = 1.5841$;
6H,6-(2-dimethylaminoethoxy-carbonyl)-8,9,10-trimethoxy-dibenzo[b,d]pyran; .HCl, m.p. 162°-165° C.;
6H,6-(2-dimethylaminoethoxy-carbonylmethyl)-dibenzo[b,d]pyran; .HCl, m.p. 136°-139° C.;
6H,6-(2-dimethylaminoethoxy-carbonylethyl)-dibenzo[b,d]pyran;
6H,6-ethoxycarbonyl-1-methoxy-dibenzo[b,d]pyran;
6H,6-ethoxycarbonyl-2-chloro-dibenzo[b,d]pyran; m.p. 49°-52° C.;
6H,6-ethoxycarbonyl-2-fluoro-dibenzo[b,d]pyran; m.p. 43°-46° C.;
6H,6-ethoxycarbonyl-2-nitro-dibenzo[b,d]pyran;
6H,6-ethoxycarbonyl-2-methoxy-dibenzo[b,d]pyran; m.p. 39°-42° C.;
6H,6-ethoxycarbonyl-2-trifluoromethyl-dibenzo[b,d]pyran;
6H,6-ethoxycarbonyl-8-chloro-dibenzo[b,d]pyran;
6H,6-ethoxycarbonyl-8-fluoro-dibenzo[b,d]pyran;
6H,6-ethoxycarbonyl-8-nitro-dibenzo[b,d]pyran;
6H,6-ethoxycarbonyl-8-methoxy-dibenzo[b,d]pyran;
6H,6-ethoxycarbonyl-1,10-dimethoxy-dibenzo[b,d]pyran;
6H,6-ethoxycarbonyl-8,9,10-trimethoxy-dibenzo[b,d]pyran; m.p. 61°-63° C.;
6H,6-ethoxycarbonyl-methyl-1-methoxy-dibenzo[b,d]pyran;
6H,6-ethoxycarbonyl-methyl-2-chloro-dibenzo[b,d]pyran; m.p. 61°-64° C.;
6H,6-ethoxycarbonyl-methyl-2-fluoro-dibenzo[b,d]pyran; m.p. 49°-52° C.;
6H,6-ethoxycarbonyl-methyl-2-nitro-dibenzo[b,d]pyran; m.p. 75°-78° C.;
6H,6-ethoxycarbonyl-methyl-2-methoxy-dibenzo[b,d]pyran; m.p. 39°-42° C.;
6H,6-ethoxycarbonyl-methyl-2-trifluoromethyl-dibenzo[b,d]pyran;
6H,6-ethoxycarbonyl-methyl-8-chloro-dibenzo[b,d]pyran;
6H,6-ethoxycarbonyl-methyl-8-fluoro-dibenzo[b,d]pyran;
6H,6-ethoxycarbonyl-methyl-8-nitro-dibenzo[b,d]pyran;
6H,6-ethoxycarbonyl-methyl-8-methoxy-dibenzo[b,d]pyran;
6H,6-ethoxycarbonyl-methyl-1,10-dimethoxy-dibenzo[b,d]pyran; m.p. 44°-47° C.;
6H,6-ethoxycarbonyl-methyl-8,9,10-trimethoxy-dibenzo[b,d]pyran; m.p. 58-61° C.;
6H,6-(2-ethoxycarbonyl-ethyl)-1-methoxy-dibenzo[b,d]pyran;
6H,6-(2-ethoxycarbonyl-ethyl)-2-chloro-dibenzo[b,d]pyran; m.p. 63°-66° C.;
6H,6-(2-ethoxycarbonyl-ethyl)-2-fluoro-dibenzo[b,d]pyran; m.p. 48°-52° C.;
6H,6-(2-ethoxycarbonyl-ethyl)-2-nitro-dibenzo[b,d]pyran;
6H,6-(2-ethoxycarbonyl-ethyl)-2-methoxy-dibenzo[b,d]pyran;
6H,6-(2-ethoxycarbonyl-ethyl)-2-trifluoromethyl-dibenzo[b,d]pyran;
6H,6-(2-ethoxycarbonyl-ethyl)-8-chloro-dibenzo[b,d]pyran;
6H,6-(2-ethoxycarbonyl-ethyl)-8-fluoro-dibenzo[b,d]pyran;
6H,6-(2-ethoxycarbonyl-ethyl)-8-nitro-dibenzo[b,d]pyran;
6H,6-(2-ethoxycarbonyl-ethyl)-8-methoxy-dibenzo[b,d]pyran;
6H,6-(2-ethoxycarbonyl-ethyl)-1,10-dimethoxy-dibenzo[b,d]pyran;
6H,6-(2-ethoxycarbonyl-ethyl)-8,9,10-trimethoxy-dibenzo[b,d]pyran; m.p. 62°-65° C.;
6H,6-(ethoxycarbonyl-hydroxy-methyl)-dibenzo[b,d]pyran,
N.M.R. CCl$_4$: δ 1 (t,3H,CH$_3$), 2.77 (bs,1H,OH), 3.95 (q,2H,CH$_2$) 6.65-7.7 (m,8H);
6H,6-(ethoxycarbonyl-hydroxy-methyl)-6-methyl-dibenzo[b,d]pyran;
6H,6-(ethoxycarbonyl-hydroxy-methyl)-2-chloro-dibenzo[b,d]pyran;
6H,6-(ethoxycarbonyl-hydroxy-methyl)-2nitro-dibenzo[b,d]pyran;
6H,6-(ethoxycarbonyl-hydroxy-methyl)-2-methoxy-dibenzo[b,d]pyran;
6H,6-(ethoxycarbonyl-hydroxy-methyl)-2-hydroxy-dibenzo[b,d]pyran;
6H,6-(ethoxycarbonyl-hydroxy-methyl)-8,9,10-trimethoxy-dibenzo[b,d]pyran;
6H,6-(N-methyl-4-piperidyloxycarbonyl)-methyl-dibenzo[b,d]pyran;
6H,6-(N-methyl-4-piperidyloxycarbonyl)-methyl-6-methyl-dibenzo[b,d]pyran;
6H,6-(3-pyridylmethylenoxycarbonyl)-methyl-dibenzo[b,d]pyran;
6H,6-(3-pyridylmethylenoxycarbonyl)-methyl-6-methyl-dibenzo[b,d]pyran.

EXAMPLE 14

A solution of 6H,6-ethoxycarbonyl-dibenzo[b,d]pyran; (5 g; 0.02 mol) in 100 ml of 32% NH$_4$OH and 50 ml of methanol was stirred in a tight stoppered flask at room temperature for ten hours. The solid 6H,6-aminocarbonyl-dibenzo[b,d]pyran was filtered (2.9 g; yield 64%); m.p. 193°-194° C.

By proceeding analogously the following compounds were obtained:
6H,6-(ter.butylaminocarbonyl-hydroxy-methyl)-dibenzo[b,d]pyran, m.p. 223°–235° C.;
6H,6-(tert.butylaminocarbonyl-hydroxy-methyl)-6-methyl-dibenzo[b,d]pyran;
6H,6-(tert.butylaminocarbonyl-hydroxy-methyl)-2-chloro-dibenzo[b,d]pyran; m.p. 207°–219° C.;
6H,6-(tert.butylaminocarbonyl-hydroxy-methyl)-2-nitro-dibenzo[b,d]pyran; m.p. 238°–246° C.;
6H,6-(tert.-butylaminocarbonyl-hydroxy-methyl)-2-methoxy-dibenzo[b,d]pyran; m.p. 195°–215° C.;
6H,6-(tert.butylaminocarbonyl-hydroxy-methyl)-2-hydroxy-dibenzo[b,d]pyran; m.p. 227°–241° C.;
6H,6-(tert.butylaminocarbonyl-hydroxy-methyl)-8,9,10-trimethoxy-dibenzo[b,d]pyran. m.p. 226°–242° C.;
6H,6-aminocarbonyl-1-methoxy-dibenzo[b,d]pyran;
6H,6-aminocarbonyl-2-chloro-dibenzo[b,d]pyran;
6H,6-aminocarbonyl-2-fluoro-dibenzo[b,d]pyran;
6H,6-aminocarbonyl-2-nitro-dibenzo[b,d]pyran;
6H,6-aminocarbonyl-2-methoxy-dibenzo[b,d]pyran;
6H,6-aminocarbonyl-2-trifluoromethyl-dibenzo[b,d]pyran;
6H,6-aminocarbonyl-8-chloro-dibenzo[b,d]pyran;
6H,6-aminocarbonyl-8-fluoro-dibenzo[b,d]pyran;
6H,6-aminocarbonyl-8-nitro-dibenzo[b,d]pyran;
6H,6-aminocarbonyl-8-methoxy-dibenzo[b,d]pyran;
6H,6-aminocarbonyl-1,10-dimethoxy-dibenzo[b,d]pyran;
6H,6-aminocarbonyl-8,9,10-trimethoxy-dibenzo[b,d]pyran;
6H,6-aminocarbonyl-6-methyl-2-chloro-dibenzo[b,d]pyran; m.p. 167°–170° C.;
6H,6-aminocarbonyl-methyl-dibenzo[b,d]pyran; m.p. 148°–150° C.;
6H,6-methylaminocarbonyl-methyl-dibenzo[b,d]pyran; m.p. 130°–131° C.;
6H,6-dimethylaminocarbonyl-methyl-dibenzo[b,d]pyran; m.p. 87°–89° C.;
6H,6-piperazinocarbonyl-methyl-dibenzo[b,d]pyran;.HCl, m.p. 224°–229° C.;
6H,6-(4-methyl-piperazinocarbonyl-methyl)-dibenzo[b,d]pyran;.HCl, m.p. 259°–262° C.
6H,6-(4-phenyl-piperazinocarbonyl-methyl)-dibenzo[b,d]pyran, m.p. 182°–186° C.

EXAMPLE 15

To a solution of 1-methyl piperazine (15.6 ml; 0.14 mol) in 200 ml of diethyl ether 6H,6-chlorocarbonyl-dibenzo[b,d]pyran (6.8 g; 28 mol) was added dropwise. After 8 hours of stirring at room temperature, the mixture was washed with water and the organic solution evaporated to dryness.

The residue was treated twice with diisopropyl ether to give 5.5 g (yield 61.4%) of 6H,6-[(4-methyl-piperazino)-carbonyl]-dibenzo[b,d]pyran, m.p. 122°–124° C.

Analogously, the following compounds were obtained:
6H,6-(ter.butylaminocarbonyl-hydroxy-methyl)-dibenzo[b,d]pyran, m.p. 223°–235° C.;
6H,6-(tert.butylaminocarbonyl-hydroxy-methyl)-6-methyl-dibenzo[b,d]pyran;
6H,6-(tert.butylaminocarbonyl-hydroxy-methyl)-2-chloro-dibenzo[b,d]pyran; m.p. 207°–219° C.;
6H,6-(tert.butylaminocarbonyl-hydroxy-methyl)-2-nitro-dibenzo[b,d]pyran; m.p. 238°–246° C.;
6H,6-(tert.-butylaminocarbonyl-hydroxy-methyl)-2-methoxy-dibenzo[b,d]pyran; m.p. 195°–215° C.;
6H,6-(tert.butylaminocarbonyl-hydroxy-methyl)-2-hydroxy-dibenzo[b,d]pyran; m.p. 227°–241° C.
6H,6-(tert.butylaminocarbonyl-hydroxy-methyl)-8,9,10-trimethoxy-dibenzo[b,d]pyran. m.p. 226°–242° C.;
6H,6-aminocarbonyl-1-methoxy-dibenzo[b,d]pyran;
6H,6-aminocarbonyl-2-chloro-dibenzo[b,d]pyran;
6H,6-aminocarbonyl-2-fluoro-dibenzo[b,d]pyran;
6H,6-aminocarbonyl-2-nitro-dibenzo[b,d]pyran;
6H,6-aminocarbonyl-2-methoxy-dibenzo[b,d]pyran;
6H,6-aminocarbonyl-2-trifluoromethyl-dibenzo[b,d]pyran;
6H,6-aminocarbonyl-8-chloro-dibenzo[b,d]pyran;
6H,6-aminocarbonyl-8-fluoro-dibenzo[b,d]pyran;
6H,6-aminocarbonyl-8-nitro-dibenzo[b,d]pyran;
6H,6-aminocarbonyl-8-methoxy-dibenzo[b,d]pyran;
6H,6-aminocarbonyl-1,10-dimethoxy-dibenzo[b,d]pyran;
6H,6-aminocarbonyl-8,9,10-trimethoxy-dibenzo[b,d]pyran;
6H-6-aminocarbonyl-6-methyl-2-chloro-dibenzo[b,d]pyran; m.p. 167°–170° C.;
6H,6-aminocarbonyl-methyl-dibenzo[b,d]pyran; m.p. 148°–150° C.;
6H,6-methylaminocarbonyl-methyl-dibenzo[b,d]pyran; m.p. 130°–131° C.;
6H,6-dimethylaminocarbonyl-methyl-dibenzo[b,d]pyran; m.p. 87°–89° C.;
6H,6-piperazinocarbonyl-methyl-dibenzo[b,d]pyran;.HCl, m.p. 224°–229° C.;
6H,6-(4-methyl-piperazinocarbonyl-methyl)-dibenzo[b,d]pyran;.HCl, m.p. 259°–262° C.
6H,6-(4-phenyl-piperazinocarbonyl-methyl)-dibenzo[b,d]pyran, m.p. 182°–186° C.

EXAMPLE 16

A solution of 6H,6-ethoxycarbonylmethyl-dibenzo[b,d]pyran (3 g; 0.011 mol) in 23% HCl (30 ml) and dioxane (15 ml) was refluxed for 10 hours.

After dilution with water, the mixture was extracted with ethyl acetate and the organic solvent was evaporated to dryness. The residue was solidified with diisopropyl ether to give 2 g (74%) of 6H,6-carboxymethyl-dibenzo[b,d]pyran; m.p. 110°–111° C.

By proceeding analogously the following compounds were obtained:
6H,6-carboxymethyl-1-methoxy-dibenzo[b,d]pyran; m.p. 87°–90° C.;
6H,6-carboxymethyl-2-chloro-dibenzo[b,d]pyran; m.p. 140°–144° C.;
6H,6-carboxymethyl-2-fluoro-dibenzo[b,d]pyran; m.p. 128°–131° C.;
6H,6-carboxymethyl-2-nitro-dibenzo[b,d]pyran;
6H,6-carboxymethyl-2-methoxy-dibenzo[b,d]pyran; m.p. 92°–95° C.;
6H,6-carboxymethyl-2-trifluoromethyl-dibenzo[b,d]pyran; m.p. 84°–87° C.;
6H,6-carboxymethyl-8-chloro-dibenzo[b,d]pyran; m.p. 131°–134° C.;
6H,6-carboxymethyl-8-fluoro-dibenzo[b,d]pyran;
6H,6-carboxymethyl-8-nitro-dibenzo[b,d]pyran; m.p. 168°–172° C.;
6H,6-carboxymethyl-8-methoxy-dibenzo[b,d]pyran; m.p,. 85°–88° C.;
6H,6-carboxymethyl-1,10-dimethoxy-dibenzo[b,d]pyran; m.p. 116°–119° C.;

6H,6-carboxymethyl-8,9,10-trimethoxy-dibenzo[b,d]pyran; m.p. 144°-147° C.;
6H,6-(2-carboxy-ethyl)-dibenzo[b,d]pyran; m.p. 104°-107° C.;
6H,6-(2-carboxy-ethyl)-1-methoxy-dibenzo[b,d]pyran;
6H,6-(2-carboxy-ethyl)-2-chloro-dibenzo[b,d]pyran; m.p. 152°-155° C.;
6H,6-(2-carboxy-ethyl)-2-fluoro-dibenzo[b,d]pyran; m.p. 132°-135° C.
6H,6-(2-carboxy-ethyl)-2-nitro-dibenzo[b,d]pyran;
6H,6-(2-carboxy-ethyl)-2-methoxy-dibenzo[b,d]pyran; m.p. 91°-94° C.;
6H,6-(2-carboxy-ethyl)-2-trifluoromethyl-dibenzo[b,d]pyran; m.p. 79°-82° C.;
6H,6-(2-carboxy-ethyl)-8-chloro-dibenzo[b,d]pyran; m.p. 158°-161° C.;
6H,6-(2-carboxy-ethyl)-8-fluoro-dibenzo[b,d]pyran;
6H,6-(2-carboxy-ethyl)-8-nitro-dibenzo[b,d]pyran; m.p. 163°-166° C.;
6H,6-(2-carboxy-ethyl)-8-methoxy-dibenzo[b,d]pyran; m.p. 90°-93° C.;
6H,6-(2-carboxy-ethyl)-1,10-dimethoxy-dibenzo[b,d]pyran; m.p. 101°-104° C.
6H,6-(2-carboxy-ethyl)-8,9,10-trimethoxy-dibenzo[b,d]pyran, m.p. 128°-131° C.

EXAMPLE 17

A solution of 6H,6-cyano-dibenzo[b,d]pyran (4 g; 0.02 mol) in 100 ml of anhydrous diethyl ether was slowly added under stirring, at room temperature, to LiAlH$_4$ (1.5 g; 0.04 mol) in 70 ml of anhydrous diethyl ether. After 20 hours the excess of LiAlH$_4$ was decomposed with water and sodium hydroxide. The suspension was filtered, the solid thoroughly washed with diethyl ether and the solvet was evaporated to dryness. The residue was taken up with 8% HCl. The obtained solution was washed with diethyl ether and then made basic with 35% NaOH. The mixture was extracted with diethyl ether. The organic solution was washed with a saturated NaCl aqueous solution and dried over sodium sulfate 6H,6-amino-methyl-dibenzo[b,d]pyran was precipitated as hydrochloride with 14% HCl alcoholic solution and crystallized from absolute ethanol: (3.5 g; yield 73%): m.p. 250° C.;

By proceeding analogously the following compounds were obtained:
6H,6-aminomethyl-1-methoxy-dibenzo[b,d]pyran;.HCl, m.p. 196°-199° C.;
6H,6-aminomethyl-2-fluoro-dibenzo[b,d]pyran;.HCl, m.p. 212°-217° C.;
6H,6-aminomethyl-2-methoxy-dibenzo[b,d]pyran;.HCl, m.p. 215°-218° C.;
6H,6-aminomethyl-2-trifluoromethyl-dibenzo[b,d]pyran;.HCl, m.p. 206°-209° C.;
6H,6-aminomethyl-8-fluoro-dibenzo[b,d]pyran;
6H,6-aminomethyl-8-methoxy-dibenzo[b,d]pyran;
6H,6-aminomethyl-1,10-dimethoxy-dibenzo[b,d]pyran;.HCl, m.p. 206°-209° C.;
6H,6-aminomethyl-8,9,10-trimethoxy-dibenzo[b,d]pyran;.HCl, m.p. 222°-224° C.

EXAMPLE 18

To a solution of 6H,6-cyano-8,9,10-trimethoxy-dibenzo[b,d]pyran (15 g, 0.051 mol.) in 100 ml of tetrahydrofurane 100 ml of a molar solution of BH$_3$ in tetrahydrofurane was slowly added at 10° C. The reacting mixture was kept at room temperature overnight; 10 ml of water and 1 ml of 37% HCl were added and the mixture was warmed at 45° C. for 2 hours. The solvent was evaporated to dryness; the residue was taken up with 2N HCl and the obtained solution was extracted several times with diethyl ether. The aqueous solution was then made basic with 35% NaOH, extracted with diethyl ether and the ether solution anhydrified. 6H,6-aminomethyl-8,9,10-trimethoxy-dibenzo[b,d]pyran was precipitated as hydrochloride with a 14% HCl alcoholic solution: (12.0 g; yield 71%): m.p. 222°-224° C.

By proceeding analogously the following compounds were prepared:
6H,6-aminomethyl-dibenzo[b,d]pyran; HCl, m.p. 250° C.
6H,6-aminomethyl-1-methoxy-dibenzo[b,d]pyran;.HCl, m.p. 196°-199° C.;
6H,6-aminomethyl-2-chloro-dibenzo[b,d]pyran;.HCl, m.p. 248°-251° C.;
6H,6-aminomethyl-2-fluoro-dibenzo[b,d]pyran;.HCl, m.p. 212°-217° C.;
6H,6-aminomethyl-2-nitro-dibenzo[b,d]pyran;
6H,6-aminomethyl-2-methoxy-dibenzo[b,d]pyran;.HCl, m.p. 215°-218° C.;
6H,6-aminomethyl-2-trifluoromethyl-dibenzo[b,d]pyran;.HCl, m.p. 206°-209° C.;
6H,6-aminomethyl-8-chloro-dibenzo[b,d]pyran;
6H,6-aminomethyl-8-fluoro-dibenzo[b,d]pyran;
6H,6-aminomethyl-8-nitro-dibenzo[b,d]pyran;
6H,6-aminomethyl-8-methoxy-dibenzo[b,d]pyran;
6H,6-aminomethyl-1,10-dimethoxy-dibenzo[b,d]pyran; HCl, m.p. 206°-209° C.

EXAMPLE 19

To a solution of 6H,6-aminocarbonyl-dibenzo[b,d]pyran (4.2 g; 0.0186 mol), in 100 ml of anhydrous tetrahydrofurane, 100 ml of a molar solution of BH$_3$ in tetrahydrofurane was added dropwise. The mixture was refluxed for 2 hours. After a warm up similar to that of example 18, 6H,6-aminomethyl-dibenzo[b,d]pyran was obtained as hydrochloride, which improved by grinding it in acetone; (3.0 g; 65%): m.p. 250° C.

By proceeding analogously the following compounds were obtained:
6H,6-aminomethyl-1-methoxy-dibenzo[b,d]pyran;.HCl, m.p. 196°-199° C.;
6H,6-aminomethyl-2-chloro-dibenzo[b,d]pyran;.HCl, m.p. 248°-251° C.;
6H,6-aminomethyl-2-fluoro-dibenzo[b,d]pyran;.HCl, m.p. 212°-217° C.
6H,6-aminomethyl-2-nitro-dibenzo[b,d]pyran;
6H,6-aminomethyl-2-methoxy-dibenzo[b,d]pyran;.HCl, m.p. 215°-218° C.;
6H,6-aminomethyl-2-trifluoromethyl-dibenzo[b,d]pyran;.HCl, m.p. 206°-209° C.;
6H,6-aminomethyl-8-chloro-dibenzo[b,d]pyran;
6H,6-aminomethyl-8-fluoro-dibenzo[b,d]pyran;
6H,6-aminomethyl-8-nitro-dibenzo[b,d]pyran;
6H,6-aminomethyl-8-methoxy-dibenzo[b,d]pyran;
6H,6-aminomethyl-1,10-dimethoxy-dibenzo[b,d]pyran;.HCl, m.p. 206°-209° C.;
6H,6-aminomethyl-8,9,10-trimethoxy-dibenzo[b,d]pyran;.HCl, m.p. 222°-224° C.;
6H,6-(2-methylamino-ethyl)-dibenzo[b,d]pyran;.HCl, m.p. 181°-182° C.;
6H,6-(3-methylamino-propyl)-dibenzo[b,d]pyran;.HCl, m.p. 143°-146° C.;
6H,6-(3-methylamino-propyl)-1-methoxy-dibenzo[b,d]pyran;

6H,6-(3-methylamino-propyl)-2-chloro-dibenzo[b,d]pyran;

6H,6-(3-methylamino-propyl)-2-fluoro-dibenzo[b,d]pyran;

6H,6-(3-methylamino-propyl)-2-nitro-dibenzo[b,d]pyran;

6H,6-(3-methylamino-propyl)-2-methoxy-dibenzo[b,d]pyran;

6H,6-(3-methylamino-propyl)-2-trifluoromethyl-dibenzo[b,d]pyran;

6H,6-(3-methylamino-propyl)-8-chloro-dibenzo[b,d]pyran;

6H,6-(3-methylamino-propyl)-8-fluoro-dibenzo[b,d]pyran;

6H,6-(3-methylamino-propyl)-8-nitro-dibenzo[b,d]pyran;

6H,6-(3-methylamino-propyl)-8-methoxy-dibenzo[b,d]pyran;

6H,6-(3-methylamino-propyl)-1,10-dimethoxy-dibenzo[b,d]pyran;

6H-6-(3-methylamino-propyl)-8,9,10-trimethoxy-dibenzo[b,d]pyran;

6H,6-(1-hydroxy-2-tert.butylamino-ethyl)-dibenzo[b,d]pyran; m.p. 101°–111° C.;

6H,6-(1-hydroxy-2-tert.butylamino-ethyl)-1-methoxy-dibenzo[b,d]pyran;.HCl, m.p. 174°–186° C.;

6H,6-(1-hydroxy-2-tert.butylamino-ethyl)-2-chloro-dibenzo[b,d]pyran;.HCl, m.p. 183°–201° C.;

6H,6-(1-hydroxy-2-tert.butylamino-ethyl)-2-fluoro-dibenzo[b,d]pyran;.HCl, m.p. 165°–178° C.;

6H,6-(1-hydroxy-2-tert.butylamino-ethyl)-2-nitro-dibenzo[b,d]pyran;

6H,6-(1-hydroxy-2-tert.butylamino-ethyl)-2-methoxy-dibenzo[b,d]pyran;.HCl, m.p. 176°–189° C.;

6H,6-(1-hydroxy-2-tert.butylamino-ethyl)-2-trifluoromethyl-dibenzo[b,d]pyran;.HCl, m.p. 181°–194° C.;

6H,6-(1-hydroxy-2-tert.butylamino-ethyl)-8-chloro-dibenzo[b,d]pyran;

6H,6-(1-hydroxy-2-tert.-butylamino-ethyl)-8-fluoro-dibenzo[b,d]pyran;

6H,6-(1-hydroxy-2-tert.butylamino-ethyl)-8-nitro-dibenzo[b,d]pyran;

6H,6-(1-hydroxy-2-tert.butylamino-ethyl)-8-methoxy-dibenzo[b,d]pyran;

6H,6-(1-hydroxy-2-tert.butylamino-ethyl)-1,10-dimethoxy-dibenzo[b,d]pyran;.HCl, m.p. 187°–206° C.;

6H,6-(1-hydroxy-2-tert.butylamino-ethyl)-8,9,10-trimethoxy-dibenzo[b,d]pyran;.HCl, m.p. 201°–218° C.

EXAMPLE 20

6H,6-(2-pyridyl)-dibenzo[b,d]pyran (2.8 g; 0.011 mol) in 60 ml of acetic acid was reduced by hydrogen in a Parr apparatus at 4 Atm, at room temperature, using $PtO_2$ (0.5 g) as a catalyst. After four hours the reaction mixture was filtered and the solvent evaporated to dryness under vacuo. The residue was taken up with a saturated $NaHCO_3$ aqueous solution and extracted with diethyl ether. The organic solution was washed with water, dried and 6H,6-(2-piperidinyl)-dibenzo[b,d]pyran was precipitated as hydrochloride with a small excess of 14% HCl alcoholic solution. The hydrochloride was taken up several times with absolute ethanol and each time the solvent was evaporated to dryness under vacuo. At the end the residue was taken up with diethyl ether and filtered: (2.5 g; yield 76%); m.p. 130° C. dec (mixture of diasteroisomers).

Analogously the following compounds were obtained:

6H,6-(3-piperidinyl)-dibenzo[b,d]pyran;.HCl, m.p. 165° C. (dec);

6H,6-(4-piperidinyl)-dibenzo[b,d]pyran;.HCl, m.p. 197°–225° C. (dec);

6H,6-(2-piperazinyl)-dibenzo[b,d]pyran.

EXAMPLE 21

6H,6-carboxy-dibenzo[b,d]pyran (46 g; 0.2 mol) was suspended in 300 ml of $SOCl_2$ and kept under stirring at room temperature for 16 hours,. After careful elimination of the excess of $SOCl_2$, the crude acid chloride was dissolved in 300 ml of anhydrous diglyme To this solution a suspension of Lithium tri.ter.butoxyaluminohydride (53.5 g; 0.21 mol) in 300 ml of diglyme was added dropwise, at a temperature of $-60°$ C. and under $N_2$ and stirring. After the addition was over, the temperature was raised to $-40°$ C. and a solution of 53.5 g of ammonium sulfate in 85 ml of water was added. At $-20°$ C. diethyl ether and decalite were added to make the suspension easier to stirr. After half an hour of vigorous stirring the suspension was filtered and the cake washed with diethyl ether. The ether was evaporated out under vacuum by keeping the external temperature not higher than 30° C. Sodium metabisulfite (54 g; 0.258 mol) in 100 ml of 80% ethanol was added to the obtained solution of aldehyde in diglyme and the whole was stirred for 16 hours. The mixture was then cooled to room temperature and KCN (13.7 g; 0.21 mol) was added all at once. After 7 hours at reflux temperature, the solution was evaporated to dryness under vacuum. The residue was taken up with diethyl ether and the obtained solution was filtered and thoroughly washed with water. After drying on sodium sulfate, the solvent was evaporated to dryness to obtain crude 6H,6-(cyano-hydroxy-methyl)-dibenzo[b,d]pyran: (32.5 g; yield 70%), as an oily light brown syrup.

By proceeding analogously the following compounds were obtained:

6H,6-(cyano-hydroxy-methyl)-6-methyl-dibenzo[b,d]pyran;

6H,6-(cyano-hydroxy-methyl)-1-methoxy-dibenzo[b,d]pyran;

6H,6-(cyano-hydroxy-methyl)-2-chloro-dibenzo[b,d]pyran;

6H,6-(cyano-hydroxy-methyl)-2-fluoro-dibenzo[b,d]pyran;

6H,6-(cyano-hydroxy-methyl)-2-nitro-dibenzo[b,d]pyran;

6H,6-(cyano-hydroxy-methyl)-2-methoxy-dibenzo[b,d]pyran;

6H,6-(cyano-hydroxy-methyl)-2-hydroxy-dibenzo[b,d]pyran;

6H,6-(cyano-hydroxy-methyl)-2-trifluoromethyl-dibenzo[b,d]pyran;

6H,6-(cyano-hydroxy-methyl)-8 -chloro-dibenzo[b,d]pyran;

6H,6-(cyano-hydroxy-methyl)-8-fluoro-dibenzo[b,d]pyran;

6H,6-(cyano-hydroxy-methyl)-8-nitro-dibenzo[b,d]pyran;

6H,6-(cyano-hydroxy-methyl)-8-methoxy-dibenzo[b,d]pyran;

6H,6-(cyano-hydroxy-methyl)-1,10-dimethoxy-dibenzo[b,d]pyran;

6H,6-(cyano-hydroxy-methyl)-8,9,10-trimethoxy-dibenzo[b,d]pyran.

EXAMPLE 22

Oxalyl chloride (11 ml; 0.125 mol) was added dropwise to a solution of 6H,6-carboxymethyl-dibenzo[b,d]pyran (15 g; 0.06 mol) in 300 ml of anhydrous benzene and 0.5 ml of anhydrous dimethylformamide. After 24 hours at room temperature the solution was evaporated to dryness and the residue was dissolved in 200 ml of diethyl ether. This solution was added, at 0°–5° C., to an ethereal solution of diazomethane (11 g) and the whole was kept at room temperature for 16 hours. After a further two hours at 40° C., nitrogen was bubbled in to remove the excess diazomethane and the solution was evaporated to dryness. The residue was dissolved in 80 ml of dioxane and to the obtained solution a mixture consisting of Ag$_2$O (4.4 g; 0.019 mol), Na$_2$S$_2$O$_3$.5H$_2$O (10.5 g; 0.042 mol) and Na$_2$CO$_3$.10H$_2$O (14 g; 0.049 mol) in 300 ml of distilled water was added at 60° C. The temperature was raised to 90° C. and maintained at this temperature for 24 hours. The reaction mixture was then poured in icy water, filtered and the aqueous solution extracted several times with diethyl ether. After acidification with 8% HCl the precipitate was extracted with ethyl acetate and the organic solution evaporated to dryness. The oily residue was taken up with diisopropyl ether to give 6H,6-(2-carboxy-ethyl)-dibenzo[b,d]pyran (8.3 g; yield 52%): m.p. 105°–107° C.

By proceeding analogously the following compounds were obtained:
6H, 6-(2-carboxy-ethyl)-6-methyl-dibenzo[b,d]pyran;
6H,6-(2-carboxy-ethyl)-6-ethyl-dibenzo[b,d]pyran;
6H,6-(2-carboxy-ethyl)-6-phenyl-dibenzo[b,d]pyran;
6H,6-(2-carboxy-ethyl)-1-methoxy-dibenzo[b,d]pyran;
6H,6-(2-carboxy-ethyl)-2-chloro-dibenzo[b,d]pyran; m.p. 152°–155° C.;
6H,6-(2-carboxy-ethyl)-2-fluoro-dibenzo[b,d]pyran; m.p. 132°–135° C.;
6H,6-(2-carboxy-ethyl)-2-nitro-dibenzo[b,d]pyran;
6H,6-(2-carboxy-ethyl)-2-methoxy-dibenzo[b,d]pyran; m.p. 91°–94° C.;
6H,6-(2-carboxy-ethyl)-2-trifluoromethyl-dibenzo[b,d]pyran; m.p. 79°–82° C.;
6H,6-(2-carboxy-ethyl)-8-chloro-dibenzo[b,d]pyran; m.p. 158°–161° C.;
6H,6-(2-carboxy-ethyl)-8-fluoro-dibenzo[b,d]pyran;
6H,6-(2-carboxy-ethyl)-8-methoxy-dibenzo[b,d]pyran; m.p. 90°–93° C.;
6H,6-(2-carboxy-ethyl)-1,10-dimethoxy-dibenzo[b,d]pyran; m.p. 101°–104° C.;
6H,6-(2-carboxy-ethyl)-8,9,10-trimethoxy-dibenzo[b,d]pyran; m.p. 128°–131° C.;
6H,6-(2-carboxy-ethyl)-6-methyl-1-methoxy-dibenzo[b,d]pyran;
6H,6-(2-carboxy-ethyl)-6-methyl-2-chloro-dibenzo[b,d]pyran;
6H,6-(2-carboxy-ethyl)-6-methyl-2-fluoro-dibenzo[b,d]pyran;
6H,6-(2-carboxy-ethyl)-6-methyl-2-nitro-dibenzo[b,d]pyran;
6H,6-(2-carboxy-ethyl)-6-methyl-2-methoxy-dibenzo[b,d]pyran;
6H,6-(2-carboxy-ethyl)-6-methyl-2-trifluoromethyl-dibenzo[b,d]pyran;
6H,6-(2-carboxy-ethyl)-6-methyl-8-chloro-dibenzo[b,d]pyran;
6H,6-(2-carboxy-ethyl)-6-methyl-8-fluoro-dibenzo[b,d]pyran;
6H,6-(2-carboxy-ethyl)-6-methyl-8-nitro-dibenzo[b,d]pyran;
6H,6-(2-carboxy-ethyl)-6-methyl-8-methoxy-dibenzo[b,d]pyran;
6H,6-(2-carboxy-ethyl)-6-methyl-1,10-dimethoxy-dibenzo[b,d]pyran;
6H,6-(2-carboxy-ethyl)-6-methyl-8,9,10-trimethoxy-dibenzo[b,d]pyran.

EXAMPLE 23

To a stirred solution of 6H,6-cyano-dibenzo[b,d]pyran (4.2 g; 0.02 mol) and CH$_3$I (28.4 g; 0.2 mol) in 100 ml of dimethylformamide, 50% NaH (1.5 g; 0.03 mol) was added in small portions. After 16 hours at room temperature the mixture was poured into water and extracted with diethyl ether. The organic phase was washed with water and dried over Na$_2$SO$_4$. Evaporation of the solvent gave 6H,6-cyano-6-methyl-dibenzo[b,d]pyran as a white solid (3.1 g; 0.014 mol; yield 70%): m.p. 114°–116° C.

By proceeding analogously the following compounds were obtained:
6H,6-cyano-6-methyl-1-methoxy-dibenzo[b,d]pyran;
6H,6-cyano-6-methyl-2-chloro-dibenzo[b,d]pyran; m.p. 112°–115° C.;
6H,6-cyano-6-methyl-2-fluoro-dibenzo[b,d]pyran; m.p. 98°–102° C.;
6H,6-cyano-6-methyl-2-nitro-dibenzo[b,d]pyran;
6H,6-cyano-6-methyl-2-methoxy-dibenzo[b,d]pyran;
6H,6-cyano-6-methyl-2-trifluoromethyl-dibenzo[b,d]pyran;
6H,6-cyano-6-methyl-8-chloro-dibenzo[b,d]pyran;
6H,6-cyano-6-methyl-8-fluoro-dibenzo[b,d]pyran;
6H,6-cyano-6-methyl-8-nitro-dibenzo[b,d]pyran;
6H,6-cyano-6-methyl-8-methoxy-dibenzo[b,d]pyran;
6H,6-cyano-6-methyl-1,10-dimethoxy-dibenzo[b,d]pyran;
6H,6-cyano-6-methyl-8,9,10-trimethoxy-dibenzo[b,d]pyran; m.p. 121°–124° C.;
6H,6-cyano-6-ethyl-dibenzo[b,d]pyran; m.p. 75°–77° C.;
6H,6-cyano-6-ethyl-1-methoxy-dibenzo[b,d]pyran;
6H,6-cyano-6-ethyl-2-chloro-dibenzo[b,d]pyran;
6H,6-cyano-6-ethyl-2-fluoro-dibenzo[b,d]pyran;
6H,6-cyano-6-ethyl-2-nitro-dibenzo[b,d]pyran; 6H,6-cyano-6-ethyl-2-methoxy-dibenzo[b,d]pyran;
6H,6-cyano-6-ethyl-2-trifluromethyl-dibenzo[b,d]pyran;
6H,6-cyano-6-ethyl-8-chloro-dibenzo[b,d]pyran;
6H,6-cyano-6-ethyl-8fluoro-dibenzo[b,d]pyran;
6H,6-cyano-6-ethyl-8-nitro-dibenzo[b,d]pyran;
6H,6-cyano-6-ethyl-8-methoxy-dibenzo[b,d]pyran;
6H,6-cyano-6-ethyl-1,10-dimethoxy-dibenzo[b,d]pyran;
6H,6-cyano-6-ethyl-8,9,10-trimethoxy-dibenzo[b,d]pyran.

EXAMPLE 24

6H,6-cyano-dibenzo[b,d]pyran (31 g; 0.15 mol) and paraformaldehyde (6 g; 0.2 mol) in 300 ml of dimethylsulphoxide was treated with a suspension of sodium methoxide (3.8 g; 0.07 mol) in dimethylsulphoxide (100 ml). The mixture was stirred for 2 hours at room temperature, then poured into water and extracted with diethyl ether. The organic phase was washed with water, dried over Na$_2$SO$_4$ and evaporated to dryness to give 6H,6-cyano-6-hydroxymethyl-dibenzo[b,d]pyran as a white solid (26.7 g; 0.11 mol; yield 75%); m.p. 106°–108° C.

By proceeding analogously the following compounds were obtained:

6H,6-cyano-6-hydroxymethyl-1-methoxy-dibenzo[b,d]pyran;
6H,6-cyano-6-hydroxymethyl-2-chloro-dibenzo[b,d]pyran; m.p. 107°–110° C.;
6H,6-cyano-6-hydroxymethyl-2-fluoro-dibenzo[b,d]pyran;
6H,6-cyano-6-hydroxymethyl-2-nitro-dibenzo[b,d]pyran;
6H, 6-cyano-6-hydroxymethyl-2-methoxy-dibenzo[b,d]pyran;
6H,6-cyano-6-hydroxymethyl-2-trifluoromethyl-dibenzo[b,d]pyran; 6H,6-cyano-6-hydroxymethyl-8-chloro-dibenzo[b,d]pyran;
6H,6-cyano-6-hydroxymethyl-8-fluoro-dibenzo[b,d]pyran;
6H,6-cyano-6-hydroxymethyl-8-nitro-dibenzo[b,d]pyran;
6H,6-cyano-6-hydroxymethyl-8-methoxy-dibenzo[b,d]pyran;
6H,6-cyano-6-hydroxymethyl-1,10-dimethoxy-dibenzo[b,d]pyran;
6H,6-cyano-6-hydroxymethyl-8,9,10-trimethoxy-dibenzo[b,d]pyran; m.p. 111°–114° C.

EXAMPLE 25

A solution of 6H,6-cyano-6-methyl-dibenzo[b,d]pyran (11.3 g; 0.05 mol) and sulfuryl chloride (25 ml; 0.3 mol) in $CHCl_3$ (120 ml) was kept on standing for 4 days at room temperature. After thorough washing with N/10 NaOH solution and water to neutrality, the solvent was evaporated under reduced pressure and the residue treated with isopropyl ether. The solid was filtered to obtain 7.5 g (60%) of 6H,6-cyano-6-methyl-2-chloro-dibenzo[b,d]pyran; m.p. 110°–112° C.

By proceeding analogously the following compounds were obtained:
6H,6-ethoxycarbonylmethyl-6-methyl-2-chloro-dibenzo[b,d]pyran;
6H,6-(2-ethoxycarbonyl-ethyl)-6-methyl-2-chloro-dibenzo[b,d]pyran.

EXAMPLE 26

6H,6-ethoxycarbonyl-2-nitro-dibenzo[b,d]pyran (4.25 g; 0.015 mol) was dissolved in 150 ml of ethanol and reduced in a Parr apparatus using 10% Pd/C as a catalyst, at room temperature and 2 Atm of pressure. After 3 hours the reaction was complete. The reaction mixture was filtered and the solvent evaporated to dryness. The oily residue was taken up with 100 ml of diethyl ether and the product was extracted with 8% HCl. The acid solution was made basic with 35% NaOH and extracted with diethyl ether. After evaporation of the solvent 6H,6-ethoxycarbonyl-2-amino-dibenzo[b,d]pyran was obtained (3.0 g; yield 78%) hydrochloride, m.p. 215°–220° C.

Analogously the following compounds were obtained:
6H,6-ethoxycarbonylmethyl-2-amino-dibenzo[b,d]pyran; .HCl, m.p. 187°–191° C.;
6H,6-ethoxycarbonylmethyl-6-methyl-2-amino-dibenzo[b,d]pyran; .HCl, m.p. 178°–182° C.;
6H,6-(2-ethoxycarbonyl-ethy)-2-amino-dibenzo[b,d]pyran;
6H,6-(2-ethoxycarbonyl-ethyl)-6-methyl-2-amino-dibenzo[b,d]pyran;
6H,6-aminomethyl-2-amino-dibenzo[b,d]pyran; m.p. 280° C.;
6H,6-(2-methylamino-ethyl)-2-amino-dibenzo[b,d]pyran;
6H,6-(3-methylamino-propyl)-2-amino-dibenzo[b,d]pyran;
6H,6-(2-dimethylamino-ethoxycarbonyl)-2-amino-dibenzo[b,d]pyran; .2HCl, m.p. 147°–150° C.;
6H,6-(2-dimethylamino-ethoxycarbony)-6-methyl-2-amino-dibenzo[b,d]pyran;
6H,6-(2-dimethylamino-ethoxycarbonylemthyl)-2-amino-dibenzo[b,d]pyran; .2HCl, m.p. 136°–139° C.;
6H,6-ethoxycarbonyl-8-amino-dibenzo[b,d]pyran;
6H,6-ethoxycarbonylmethyl-8-amino-dibenzo[b,d]pyran;
6H,6-ethoxycarbonylmenthyl-6-methyl-8-amino-dibenzo[b,d]pyran;
6H,6-(2-ethoxycarbonyl-ethyl)-8-amino-dibenzo[b,d]pyran;
6H,6-(2-ethoxycarbonyl-ethyl)-6-methyl-8-amino-dibenzo[b,d]pyran;
6H,6-methylamino-8-amino-dibenzo[b,d]pyran;
6H,6-(2-methylamino-ethyl)-8-amino-dibenzo-dibenzo[b,d]pyran;
6H,6-(3-methylamino-propyl)-8-amino-dibenzo[b,d]pyran;
6H,6-(2-dimethylamino-ethoxycarbonyl)-8-amino-dibenzo[b,d]pyran;
6H,6-(2-dimethylamino-ethoxycarbonyl)-6-methyl-8-amino-dibenzo[b,d]pyran;
6H,6-(2-dimethylamino-ethoxycarbonylemthyl)-8-amino-dibenzo[b,d]pyran.

EXAMPLE 27

By keeping the temperature at $-5°/0°$ C., $NaNO_2$ (1.4 g; (0.02 mol) dissolved in distilled water (30 ml) was added drop by drop to a solution of 6H,6-cyano-2-aminodibenzo[b,d]pyran (4.5 g; 0.02 mol) in 23% HCl (8.4 ml), under stirring. Then the temperature of the reaction mixture was allowed to rise to about 20° C. The mixture, after stirring for 24 hours, was diluted with water, basified to pH 9–10 by adding NaOH and then washed with diethyl ether. The crude product was acidified, extracted with ethyl acetate, washed again dried on anhydrous $Na_2SO_4$, and decolorised. The solvent was evaporated to dryness thus giving 6H,6-cyano-2-hydroxy-dibenzo[b,d]pyran as a whitish solid (3.6 g; 0.016 mol; yield 80%; m.p. 146°–148° C.).

By proceeding analogously the following compounds were obtained:
6H,6-ethoxycarbonyl-2-hydroxy-dibenzo[b,d]pyran; m.p. 79°–82° C.;
6H,6-ehoxycarbonylmethyl-2-hydroxy-dibenzo[b,d]pyran; m.p. 75°–79° C.;
6H,6-ethoxycarbonylmethyl-6-methyl-2-hydroxy-dibenzo[b,d]pyran, m.p. 74°–77° C.
6H,6-(2-ethoxycarbonyl-ethyl)-2-hydroxy-dibenzo[b,d]pyran;
6H,6-(2-ethoxycarbonyl-ethyl-6-methyl-2-hydroxy-dibenzo[b,d]pyran;
6H,6-(2-dimethylamino-ethoxycarbonyl)-2-hydroxy-dibenzo[b,d]pyran; .HCl, m.p. 179°–182° C.;
6H,6-(2-dimethylamino-ethoxycarbonyl)-6-methyl-2-hydroxy-dibenzo[b,d]pyran; .HCl, m.p. 168°–171° C.;
6H,6-(2-dimethylamino-ethoxycarbonylmethyl)-2-hydroxy-dibenzo[b,d]pyran; .HCl, m.p. 152°–155° C.;
6H,6-ethoxycarbonyl-8-hydroxy-dibenzo[b,d]pyran;

6H,6-ethoxycarbonylmethyl-8-hydroxy-dibenzo[b,d]pyran;
6H,6-ethoxycarbonylmethyl-6-methyl-8-hydroxy-diibenzo[b,d]pyran;
6H,6-(2-ethoxycarbonyl-ethyl)-8-hydroxy-dibenzo[b,d]pyran;
6H,6-(2-ethoxycarbonyl-ethyl)-6-methyl-8hydroxy-dibenzo[b,d]pyran;
6H,6-(2-dimethylamino-ethoxycarbonyl)-8-hydroxy-dibenzo[b,d]pyran;
6H,6-(2-dimethylamino-ethoxycarbonyl)-6-methyl-8-hydroxy-dibenzo[b,d]pyran;
6H,6-(2-dimethylamino-ethoxycarbonylmethyl)-8-hydroxy-dibenzo[b,d]pyran.

EXAMPLE 28

To a solution of 6H,6-aminomethyl-2-methoxy-dibenzo[b,d]pyran (2.4 g; 0.01 mol) in 50 ml of anhydrous CH$_2$Cl$_2$ a solution of BBr$_3$ (5.6 g; 0.0225 mol) in 100 ml of anhydrous CH$_2$Cl$_2$ was added dropwise, at a temperature of $-20°$ C. After two hours the temperature was left to raise spontaneouly to 0° C. and 150 ml of water were added cautiously. After one hour under stirring the aqueous layer was separated, washed with ethyl acetate and then saturated with sodium bicarbonate. The solution was extracted with ethyl acetate.

After drying on sodium sulphate, 6H,6-aminomethyl-2-hydroxy-dibenzo[b,d]pyran was obtained by eliminating the solvent under vacuo: (1.2 g; yield 53%): hydrochloride m.p. 279°–282° C.

Analogously the following compounds were obtained:
6H,6-cyano-1-hydroxy-dibenzo[b,d]pyran;
6H,6-ethoxycarbonyl-1-hydroxy-dibenzo[b,d]pyran;
6H,6-ethoxycarbonylmethyl-1-hydroxy-dibenzo[b,d]pyran;
6H,6-ethoxycarbonylmethyl-6-methyl-1-hydroxy-dibenzo[b,d]pyran;
6H,6-(2-ethoxycarbonyl-ethyl)-1-hydroxy-dibenzo[b,d]pyran;
6H,6-(2-ethoxycarbonyl-ethyl)-6-methyl-1-hydroxy-dibenzo[b,d]pyran;
6H,6-(2-methylamino-ethyl)-1-hydroxy-dibenzo[b,d]pyran;
6H,6-(3-methylamino-propyl)-1-hydroxy-dibenzo[b,d]pyran;
6H,6-(2-dimethylamino-ethoxycarbonyl)-1-hydroxy-dibenzo[b,d]pyran;
6H,6-(2-dimethylamino-ethoxycarbonyl)-6-methyl-1-hydroxy-dibenzo[b,d]pyran;
6H,6-(2-dimethylamino-ethoxycarbonylmethyl)-1-hydroxy-dibenzo[b,d]pyran;
6H,6-cyano-2-hydroxy-dibenzo[b,d]pyran;
6H,6-ethoxycarbonyl-2-hydroxy-dibenzo[b,d]pyran;
6H,6-ethoxycarbonylmethyl-2-hydroxy-dibenzo[b,d]pyran;
6H,6-ethoxycarbonylmethyl-6-methyl-2-hydroxy-dibenzo[b,d]pyran;
6H,6-(2-ethoxycarbonyl-ethyl)-2-hydroxy-dibenzo[b,d]pyran;
6H,6-(2-ethoxycarbonyl-ethyl)-6-methyl-2-hydroxy-dibenzo[b,d]pyran;
6H,6-(2-dimethylamino-ethoxycarbonyl)-2-hydroxy-dibenzo[b,d]pyran;
6H,6-(2-dimethylamino-ethoxycarbonyl)-6-methyl-2-hydroxy-dibenzo[b,d]pyran;
6H,6-(2-dimethylamino-ethoxycarbonylmethyl)-2-hydroxy-dibenzo[b,d]pyran;
6H,6-cyano-8-hydroxy-dibenzo[b,d]pyran;
6H,6-ethoxycarbonyl-8-hydroxy-dibenzo[b,d]pyran;
6H,6-ethoxycarbonylmethyl-8-hydroxy-dibenzo[b,d]pyran;
6H,6-ethoxycarbonylmethyl-6-methyl-8-hydroxy-dibenzo[b,d]pyran;
6H,6-(2-ethoxycarbonyl-ethyl)-8-hydroxy-dibenzo[b,d]pyran;
6H,6-(2-ethoxycarbonyl-ethyl)-6-methyl-8-hydroxy-dibenzo[b,d]pyran;
6H,6-methylamino-8-hydroxy-dibenzo[b,d]pyran;
6H,6-(2-methylamino-ethyl)-8-hydroxy-dibenzo[b,d]pyran;
6H,6-(3-methylamino-propyl)-8-hydroxy-dibenzo[b,d]pyran;
6H,6-(2-dimethylamino-ethoxycarbonyl)-8-hydroxy-dibenzo[b,d]pyran;
6H,6-(2-dimethylamino-ethoxycarbonyl)-6-methyl-8-hydroxy-dibenzo[b,d]pyran;
6H,6-(2-dimethylamino-ethoxycarbonylmethyl)-8-hydroxy-dibenzo[b,d]pyran.

EXAMPLE 29

6H,6-carboxy-dibenzo[b,d]pyran (46 g; 0.2 mol) was suspended in 300 ml of SOCl$_2$ and kept under stirring at room temperature for 16 hours. After careful elimination of the excess of SOCl$_2$, the crude acid chloride was dissolved in 300 ml of anhydrous diglyme. To this solution a suspension of Lithium tri.ter.butoxyaluminohydride (53.5 g; 0.21 mol) in 300 ml of diglyme was added dropwise, at a temperature of $-60°$ C. and under N$_2$ and stirring. After the addition was over, the temperature was raised to $-40°$ C. and a solution of 53.5 g of ammonium sulfate in 85 ml of water was added. At $-20°$ C. diethyl ether and decalite were added to make the suspension easier to stirr. After half an hour of vigorous stirring the suspension was filtered and the cake washed with diethyl ether. The ether was evaporated out under vacuum by keeping the external temperature not higher than 30° C.

A solution of ammonium chloride (13 g; 0.24 mol) in 30 ml of water was added under stirring to the obtained solution of the aldehyde in diglyme. A solution of sodium cyanide (8.6 g; 0.22 mol) in 20 ml of water was added keeping the temperature below 15° C. After 16 hours at room temperature the solution was evaporated under vacuum. The residue was dissolved in 100 ml of methanol and saturated with ammonia gas at 0° C. The mixture was allowed to stand for 2 days in a stoppered flask. The residue was taken up with diethyl ether and the obtained solution was filtered and thoroughly washed with water.

After anhydrification on sodium sulfate, the solvent was evaporated to dryness. The crude product was treated with ethanolic hydrogen chloride and precipitated from diethyl ether to give 6H,6-(cyano-aminomethyl)-dibenzo[b,d]pyran hydrochloride (10.2 g; yield 21%) m.p. 96°–109° C.

By proceeding analogously the following compounds were obtained:
6H,6-(cyano-aminomethyl)-6-methyl-dibenzo[b,d]pyran;
6H,6-(cyano-aminomethyl)-1-methoxy-dibenzo[b,d]pyran;
6H,6-(cyano-aminomethyl)-2-chloro-dibenzo[b,d]pyran; .HCl; m.p. 102°–120° C.;
6H,6-(cyano-aminomethyl)-2-fluoro-dibenzo[b,d]pyran;
6H,6-(cyano-aminomethyl)-2-nitro-dibenzo[b,d]pyran; .HCl; m.p. 87°–111° C.;

6H,6-(cyano-aminomethyl)-2-methoxy-dibenzo[b,d]pyran;
6H,6-(cyano-aminomethyl)-2-hydroxy-dibenzo[b,d]pyran;
6H,6-(cyano-aminomethyl)-2-trifluoromethyl-dibenzo[b,d]pyran;
6H,6-(cyano-aminomethyl)-8-chloro-dibenzo[b,d]pyran;
6H,6-(cyano-aminomethyl)-8-fluoro-dibenzo[b,d]pyran;
6H,6-(cyano-aminomethyl)-8-nitro-dibenzo[b,d]pyran;
6H,6-(cyano-aminomethyl)-8-methoxy-dibenzo[b,d]pyran;
6H,6-(cyano-aminomethyl)-1,10-dimethoxy-dibenzo[b,d]pyran;
6H,6-(cyano-aminomethyl)-8,9,10-trimethoxy-dibenzo[b,d]pyran.

EXAMPLE 30

A solution of NaOH drops (0.8 g; 0.02 mol) in methyl alcohol (10 ml) was added to a solution of 6H,6-carboxy-6-methyl-2-chloro-dibenzo[b,d]pyran (5.5 g; 0.02 mol) in methyl alcohol (100 ml). The solvent was evaporated off and the residue taken up with 99% ethyl alcohol. The solvent was evaporated, the residue taken up with 99% ethyl alcohol and the solvent evaporated again, thus giving 6H,6-carboxy-6-methyl-2-chloro-dibenzo[b,d]pyran sodium salt (5.9 g; 0.02 mol; yield 100%); m.p. >250° C.

Analogously the following compounds were obtained:
6H,6-carboxymethyl-dibenzo[b,d]pyran sodium salt;
6H,6-carboxymethyl-6-methyl-dibenzo[b,d]pyran sodium salt;
6H,6-(2-carboxy-ethyl)-dibenzo[b,d]pyran sodium salt.

EXAMPLE 31

In an anhydrous reaction apparatus, under nitrogen atmosphere, 6H-dibenzo[b,d]pyran-6-one (30 g; 0.15 mol) was dissolved in anhydrous toluene (100 ml). The mixture was cooled to −60° C. and a 1.2M solution of diisobutylaluminium hydride (DIBAH) in toluene (150 ml) was added. The temperature was kept at −60° C. for 2 hours then water (150 ml) and decalite (3 g) were added; the mixture was filtered and the residue was washed with toluene. The organic layer was separated, washed with water, dried over anhydrous Na$_2$SO$_4$ and finally evaporated to dryness to give a semisolid product, which was crystallized from n-hexane; 6H,6-hydroxy-dibenzo[b,d]pyran (21 g; 0.106 mol; yield 70%) was obtained as white solid; m.p. 89°–91° C.

By proceeding analogously the following compounds were obtained:
6H,6-hydroxy-1-methoxy-dibenzo[b,d]pyran;
6H,6-hydroxy-2-chloro-dibenzo[b,d]pyran;
6H,6-hydroxy-2-fluoro-dibenzo[b,d]pyran;
6H,6-hydroxy-2-nitro-dibenzo[b,d]pyran;
6H,6-hydroxy-2-methoxy-dibenzo[b,d]pyran;
6H,6-hydroxy-2-trifluoromethyl-dibenzo[b,d]pyran;
6H,6-hydroxy-8-chloro-dibenzo[b,d]pyran;
6H,6-hydroxy-8-fluoro-dibenzo[b,d]pyran;
6H,6-hydroxy-8-methoxy-dibenzo[b,d]pyran;
6H,6-hydroxy-1,10-dimethoxy-dibenzo[b,d]pyran;
6H,6-hydroxy-8,9,10-trimethoxy-dibenzo[b,d]pyran.

EXAMPLE 32

To a solution of 6H-dibenzo[b,d]pyran-6-one (30 g; 0.153 mol), in a mixture of 250 ml of anhydrous diethyl ether and 250 ml of anhydrous benzene, an ethanol solution of Grignard reagent prepared from bromobenzene (23 ml; 0.23 mol) was added dropwise at 0° C. The temperature was left to reach the room temperature and the solution was stirred for a further 2 hours. After washing with 1N HCl and with water to neutrality, evaporation under vacuo of the solvent gave 6H,6-hydroxy-6-phenyl-dibenzo[b,d]pyran (39.3 g; yield 94%) as a light yellow oil.

By proceeding analogously the following compounds were obtained:
6H,6-hydroxy-6-phenyl-1-methoxy-dibenzo[b,d]pyran;
6H,6-hydroxy-6-phenyl-2-chloro-dibenzo[b,d]pyran;
6H,6-hydroxy-6-phenyl-2-fluoro-dibenzo[b,d]pyran;
6H,6-hydroxy-6-phenyl-2-nitro-dibenzo[b,d]pyran;
6H,6-hydroxy-6-phenyl-2-methoxy-dibenzo[b,d]pyran;
6H,6-hydroxy-6-phenyl-2-trifluoromethyl-dibenzo[b,d]pyran;
6H,6-hydroxy-6-phenyl-8-chloro-dibenzo[b,d]pyran;
6H,6-hydroxy-6-phenyl-8-fluoro-dibenzo[b,d]pyran;
6H,6-hydroxy-6-phenyl-8-nitro-dibenzo[b,d]pyran;
6H,6-hydroxy-6-phenyl-8-methoxy-dibenzo[b,d]pyran;
6H,6-hydroxy-6-phenyl-1,10-dimethoxy-dibenzo[b,d]pyran;
6H,6-hydroxy-6-phenyl-8,9,10-trimethoxy-dibenzo[b,d]pyran.

FORMULATION EXAMPLES

Formulation 1: Tablet (50 mg)

Tablets, each weighing 150 mg and containing 50 mg of the active substance are manufactured as follows:

| Composition (for 10,000 tablets) | |
|---|---|
| 6H,6-carboxy-6-methyl-2-chloro-dibenzo[b,d]pyran | 500 g |
| Lactose | 710 g |
| Corn starch | 237.5 g |
| Talc powder | 37.5 g |
| Magnesium stearate | 15 g |

6H,6-carboxy-6-methyl-2-chloro-dibenzo[b,d]pyran, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed, and processed into tablets using punches of 8 mm diameter.

Formulation 2: intramuscular injection

An injectable pharmaceutical composition was manufactured by dissolving 150–500 mg of 6H,6-carboxy-6-methyl-2-chloro-dibenzo[b,d]pyran sodium salt in sterile water or sterile normal saline solution (1–2 ml).

Analogously, injectable pharmaceutical compositions containing the compounds previously described in the preceding examples were prepared.

Formulation 3: Capsules (50 mg)

| | |
|---|---|
| 6H,6-ethoxycarbonyl-6-methyl-2-chloro-dibenzo[b,d]pyran | 50 |
| Lactose | 298 |
| Corn starch | 50 |
| Magnesium stearate | 2 |
| Total | 400 mg |

Encapsulate in two-piece hard gelatin capsules.

| Formulation 4: Suppository (50 mg) | g/g |
|---|---|
| 6H,6-carboxy-6-methyl-2-chloro-dibenzo[b,d]pyran | 0.05 |
| Lecithin | 0.07 |
| Cocoa butter | 0.88 |
| Total | 1.00 g |

| Formulation 5: Cream | mg/g |
|---|---|
| 6H,6-carboxy-6-methyl-2-chloro-dibenzo[b,d]pyran | 50.0 |
| White petrolatum | 100.0 |
| Cetylstearyl alcohol | 72.0 |
| Mineral oil | 60.0 |
| Polypropylene glycol | 22.5 |
| 4-Chloro-m-cresol | 1.0 |
| Purified water to make | 1.0 g |

| Formulation 6: Ointment | mg/g |
|---|---|
| 6H,6-carboxy-6-methyl-2-chloro-dibenzo[b,d]pyran | 50.0 |
| Mineral oil | 50.0 |
| Propylene glycol | 50.0 |
| Petrolatum, to make | 1.0 g |

Formulation 7: Syrup

| 6H,6-carboxy-6-methyl-2-chloro-dibenzo[b,d]pyran sodium salt | 0.5 g |
|---|---|
| Gum tragacanth | 1.0 g |
| Methyl-p-hydroxybenzoate | 0.135 g |
| Propyl p-hydroxybenzoate | 0.015 g |
| Polyoxymethylene sorbitan monolaurate | 5 g |
| Glycerine 30 Be | 5 g |
| Saccharose | 50 g |
| Natural Flavour | q.s. |
| Purified water to make | 100 ml |

We claim:

1. A compound of general formula (I)

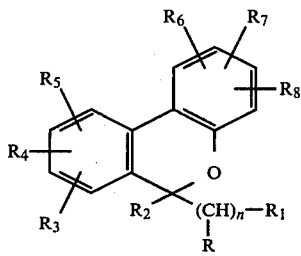

wherein $R_1$ represents (a) cyano; (b) a carboxy group, or an esterified carboxy group of the formula $-COOR_{10}$, wherein $R_{10}$ is

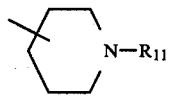

wherein $R_{11}$ is hydrogen, methyl or ethyl; or $R_{10}$ is $C_1$–$C_6$ alkyl optionally substituted by (a''')

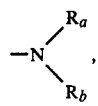

wherein $R_a$ and $R_b$ are as defined below,

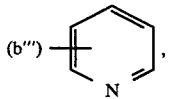

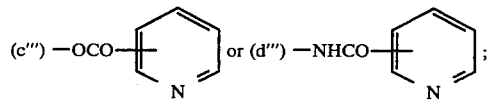

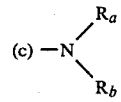

wherein each of $R_a$ and $R_b$, being the same or different, is hydrogen or unsubstituted $C_1$–$C_6$ alkyl, or $R_a$ and $R_b$, taken together with the nitrogen atom to which they are linked, form a heteromonocyclic ring selected from the group consisting of pyrrole, pyrazole, imidazole, dihydropyridine, dihydropyrazine, 1,4-oxazine, 1,4-thiazine, pyrrolidine, piperidine, piperazine, morpholine and thiomorpholine, optionally substituted by $C_1$–$C_6$ alkyl or phenyl; (d)

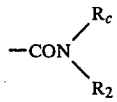

wherein each of $R_c$ and $R_d$, being the same or different, is hydrogen or $C_1$–$C_6$ alkyl unsubstituted or substituted by

wherein $R_a$ and $R_b$ are as defined above, or $R_c$ and $R_d$, taken together with the nytrogen atoms to which they are linked, form a heteromonocyclic ring selected from the group consisting of pyrrole, pyrazole, imidazole, dihydropyridine, dihydropyrazine, 1,4-oxazine, 1,4-thiazine, pyrrolidine, piperidine, piperazine, morpholine and thiomorpholine, optionally substituted by $C_1$–$C_6$ alkyl or phenyl; (e) a saturated or unsaturated 5- or 6-membered heterocyclic ring bound to the alkyl group or to the benzopyrane system through a carbon-carbon linkage, said 5- or 6-membered heterocyclic ring being selected from the group consisting of pyridyl, piperidyl, piperazinyl and pyrazinyl, which ring is unsubstituted or optionally substituted by $C_1$–$C_6$ alkyl or phenyl;

R is hydrogen; hydroxy or amino;

n is zero, 1, 2 or 3;

$R_2$ represents hydrogen; $C_1$–$C_6$ alkyl optionally substituted by hydroxy or by a $-OCO-C_1$–$C_6$ alkyl group; or a phenyl group optionally substituted by one or more of fluorine, chlorine, hydroxy and methoxy;

each of $R_3$, $R_4$, $R_5$, $R_6$, $R_7$ and $R_8$, which may be the same or different, is selected from (a'') hydrogen;

halogen; halo-$C_1$-$C_6$ alkyl; or $C_1$-$C_6$ alkyl optionally substituted by amino; (b″) amino; nitro; or

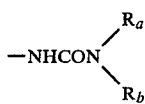

wherein $R_a$ and $R_b$ are as defined above (c″) —$OR_9$, wherein $R_9$ is hydrogen, $C_1$-$C_6$ alkyl or $C_2$-$C_6$ alkenyl; and the pharmaceutically or veterinarily acceptable salts thereof.

2. A compound of formula (I) according to claim 1 wherein:
R is hydrogen, hydroxy or amino;
$R_1$ is a free carboxy group or an esterified carboxy group of formula —$COOR'_{10}$, wherein $R'_{10}$ is ($a^{IV}$) $C_1$-$C_4$ alkyl, unsubstituted or substituted by a group

wherein $R_a$ and $R_b$ are as defined in claim 1, or by a group —(OCO)$_X$—Py, wherein X is zero or 1 and Py is pyridyl; or ($b^{IV}$) an unsubstituted or methyl- or ethyl-substituted piperidyl group; or $R_1$ is

wherein $R_a$ and $R_b$ are as defined in claim 1, or

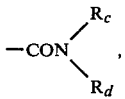

wherein $R_c$ and $R_d$ are as defined in claim 1;
$R_2$ is hydrogen, methyl, hydroxymethyl or unsubstituted phenyl;
each of $R_3$, $R_4$ and $R_5$ is, independently, hydrogen, chlorine, fluorine, trifluoromethyl, $C_1$-$C_4$ alkyl, nitro, amino or a group —O $R'_9$ wherein $R'_9$ is hydrogen or $C_1$-$C_4$ alkyl;
each of $R_6$, $R_7$ and $R_8$ is, independently, hydrogen, halogen, nitro, amino;

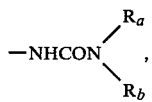

wherein $R_a$ and $R_b$ are as defined in claim 1;
or a group —O $R'_9$, wherein $R'_9$ is as defined above;
n is zero, 1 or 2; and the pharmaceutically or veterinarily acceptable salts thereof.

3. A compound of formula (I) according to claim 1 wherein:
R is hydrogen, hydroxy or amino
$R_1$ is —COOH, —$COOC_2H_5$, —$COOCH(CH_3)_2$,

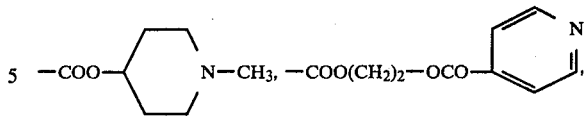

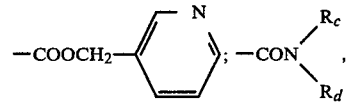

wherein $R_c$ and $R_d$ are as defined in claim 1;

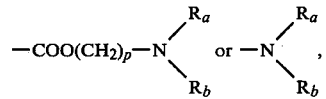

wherein p is 2 or 3 and $R_a$ and $R_b$ are as defined in claim 1;
$R_2$ is hydrogen, —$CH_3$, —$CH_2OH$ or unsubstituted phenyl;
each of $R_3$, $R_4$ and $R_5$ is, independently, hydrogen, chlorine, fluorine, methyl, hydroxy, $C_1$-$C_4$ alkoxy, amino or nitro;
each of $R_6$, $R_7$ and $R_8$ is, independently, fluorine, chlorine, bromine, hydrogen, hydroxy, $C_1$-$C_4$ alkoxy, nitro, amino or

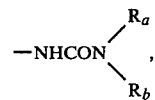

wherein $R_a$ and $R_b$ are as defined in claim 1;
n is zero, 1 or 2; and the pharmaceutically or veterinarily acceptable salts thereof.

4. A compound selected from the group consisting of:
6H,6-cyano-dibenzo[b,d]pyran;
6H,6-cyano-1-methoxy-dibenzo[b,d]pyran;
6H,6-cyano-2-chloro-dibenzo[b,d]pyran;
6H,6-cyano-2-fluoro-dibenzo[b,d]pyran;
6H,6-cyano-2-nitro-dibenzo[b,d]pyran;
6H,6-cyano-2-methoxy-dibenzo[b,d]pyran;
6H,6-cyano-1,10-dimethoxy-dibenzo[b,d]pyran;
6H,6-cyano-8,9,10-trimethoxy-dibenzo[b,d]pyran;
6H,6-cyano-6-methyl-dibenzo[b,d]pyran;
6H,6-cyano-6-methyl-2-chloro-dibenzo[b,d]pyran;
6H,6-cyano-6-methyl-2-fluoro-dibenzo[b,d]pyran;
6H,6-cyano-6-methyl-1,10-dimethoxy-dibenzo[b,d]pyran;
6H,6-cyano-6-methyl-8,9,10-trimethoxy-dibenzo[b,d]pyran;
6H,6-(1-piperazinyl)-dibenzo[b,d]pyran;
6H,6-(1-piperazinyl)-2-chloro-dibenzo[b,d]pyran;
6H,6-(1-piperazinyl)-2-fluoro-dibenzo[b,d]pyran;
6H,6-(1-piperazinyl)-2-nitro-dibenzo[b,d]pyran;
6H,6-(1-piperazinyl)-2-methoxy-dibenzo[b,d]pyran;
6H,6-(1-piperazinyl)-1,10-dimethoxy-dibenzo[b,d]pyran;
6H,6-(1-piperazinyl)-8,9,10-trimethoxy-dibenzo[b,d]pyran;
6H,6-ethoxycarbonyl-dibenzo[b,d]pyran;
6H,6-ethoxycarbonyl-1-methoxy-dibenzo[b,d]pyran;
6H,6-ethoxycarbonyl-2-hydroxy-dibenzo[b,d]pyran;
6H,6-ethoxycarbonyl-2-chloro-dibenzo[b,d]pyran;

6H,6-ethoxycarbonyl-6-methyl-2-chloro-dibenzo[b,d]pyran;
6H,6-ethoxycarbonyl-2-amino-dibenzo[b,d]pyran;
6H,6-ethoxycarbonyl-6-methyl-dibenzo[b,d]pyran;
6H,6-ethoxycarbonylmethyl-dibenzo[b,d]pyran;
6H,6-ethoxycarbonylmethyl-2-chloro-dibenzo[b,d]pyran;
6H,6-ethoxycarbonylmethyl-2-fluoro-dibenzo[b,d]pyran;
6H,6-ethoxycarbonylmethyl-2-nitro-dibenzo[b,d]pyran;
6H,6-ethoxycarbonylmethyl-2-amino-dibenzo[b,d]pyran;
6H,6-ethoxycarbonylmethyl-2-methoxy-dibenzo[b,d]pyran;
6H,6-ethoxycarbonylmethyl-2-hydroxy-dibenzo[b,d]pyran;
6H,6-ethoxycarbonylmethyl-1,10-dimethoxy-dibenzo[b,d]pyran;
6H,6-ethoxycarbonylmethyl-8,9,10-trimethoxy-dibenzo[b,d]pyran;
6H,6-ethoxycarbonylmethyl-6-methyl-dibenzo[b,d]pyran;
6H,6-ethoxycarbonylmethyl-6-methyl-2-chloro-dibenzo[b,d]pyran;
6H,6-ethoxycarbonylmethyl-6-methyl-2-fluoro-dibenzo[b,d]pyran;
6H,6-ethoxycarbonylmethyl-6-methyl-2-nitro-dibenzo[b,d]pyran;
6H,6-ethoxycarbonylmethyl-6-methyl-2-amino-dibenzo[b,d]pyran;
6H,6-ethoxycarbonylmethyl-6-methyl-2-methoxy-dibenzo[b,d]pyran;
6H,6-ethoxycarbonylmethyl-6-methyl-2-hydroxy-dibenzo[b,d]pyran;
6H,6-(2-ethoxycarbonylethyl)-dibenzo[b,d]pyran;
6H,6-(2-ethoxycarbonylethyl)-2-chloro-dibenzo[b,d]pyran;
6H,6-(2-ethoxycarbonylethyl)-2-fluoro-dibenzo[b,d]pyran;
6H,6-(2-ethoxycarbonylethyl)-8,9,10-trimethoxy-dibenzo[b,d]pyran;
6H,6-(2-ethoxycarbonylethyl)-6-methyl-dibenzo[b,d]pyran;
6H,6-(2-dimethylaminoethoxy-carbonyl)-2-chloro-dibenzo[b,d]pyran;
6H,6-(2-dimethylaminoethoxy-carbonyl)-2-fluoro-dibenzo[b,d]pyran;
6H,6-(2-dimethylaminoethoxy-carbonyl)-2-nitro-dibenzo[b,d]pyran;
6H,6-(2-dimethylaminoethoxy-carbonyl)-2-methoxy-dibenzo[b,d]pyran;
6H,6-(2-dimethylaminoethoxy-carbonyl)-2-hydroxy-dibenzo[b,d]pyran;
6H,6-(2-dimethylaminoethoxy-carbonyl)-2-amino-dibenzo[b,d]pyran;
6H,6-(2-dimethylaminoethoxy-carbonyl)-1,10-dimethoxy-dibenzo[b,d]pyran;
6H,6-(2-dimethylaminoethoxy-carbonyl)-8,9,10-trimethoxy-dibenzo[b,d]pyran;
6H,6-(2-dimethylaminoethoxy-carbonyl)-6-methyl-dibenzo[b,d]pyran;
6H,6-(2-dimethylaminoethoxy-carbonyl)-6-ethyl-dibenzo[b,d]pyran;
6H,6-(2-dimethylamino-ethoxy-carbonyl)-6-methyl-2-hydroxy-dibenzo[b,d]pyran;
6H,6-(2-dimethylamino-ethoxy-carbonyl)-6-methyl-2-amino-dibenzo[b,d]pyran;
6H,6-(2-dimethylaminoethoxy-carbonylmethyl)-dibenzo[b,d]pyran;
6H,6-(3-pyridylmethylenoxy-carbonylmethyl)-dibenzo[b,d]pyran;
6H,6-(3-pyridylmethylenoxy-carbonylmethyl)-6-methyl-dibenzo[b,d]pyran;
6H,6-carboxy-6-methyl-2-chloro-dibenzo[b,d]pyran;
6H,6-carboxy-6-methyl-2-fluoro-dibenzo[b,d]pyran;
6H,6-carboxy-6-methyl-2-nitro-dibenzo[b,d]pyran;
6H,6-carboxy-6-methyl-2-methoxy-dibenzo[b,d]pyran;
6H,6-carboxy-6-methyl-2-trifluoromethyl-dibenzo[b,d]pyran;
6H,6-carboxy-6-methyl-1,10-dimethoxy-dibenzo]b,d]pyran;
6H,6-carboxy-8,9,10-trimethoxy-dibenzo[b,d]pyran;
6H,6-carboxymethyl-dibenzo[b,d]pyran;
6H,6-carboxymethyl-1-methoxy-dibenzo[b,d]pyran;
6H,6-carboxymethyl-2-chloro-dibenzo[b,d]pyran;
6H,6-carboxymethyl-2-fluoro-dibenzo[b,d]pyran;
6H,6-carboxymethyl-2-nitro-dibenzo[b,d]pyran;
6H,6-carboxymethyl-2-methoxy-dibenzo[b,d]pyran;
6H,6-carboxymethyl-2-trifluoromethyl-dibenzo[b,d]pyran;
6H,6-carboxymethyl-8-chloro-dibenzo[b,d]pyran;
6H,6-carboxymethyl-8-fluoro-dibenzo[b,d]pyran;
6H,6-carboxymethyl-8-nitro-dibenzo[b,d]pyran;
6H,6-carboxymethyl-8-methoxy-dibenzo[b,d]pyran;
6H,6-carboxymethyl-1,10-dimethoxy-dibenzo[b,d]pyran;
6H,6-carboxymethyl-8,9,10-trimethoxy-dibenzo[b,d]pyran;
6H,6-carboxymethyl-6-methyl-dibenzo[b,d]pyran;
6H,6-(2-carboxyethyl)-dibenzo[b,d]pyran;
6H,6-(2-carboxy-ethyl)-2-chloro-dibenzo[b,d]pyran;
6H,6-(2-carboxy-ethyl)-2-fluoro-dibenzo[b,d]pyran;
6H,6-(2-carboxy-ethyl)-2-nitro-dibenzo[b,d]pyran;
6H,6-(2-carboxy-ethyl)-2-methoxy-dibenzo[b,d]pyran;
6H,6-(2-carboxy-ethyl)-1,10-dimethoxy-dibenzo[b,d]pyran;
6H,6-(2-carboxy-ethyl)-8,9,10-trimethoxy-dibenzo[b,d]pyran;
6H,6-amino-methyl-dibenzo[b,d]pyran;
6H,6-amino-methyl-2-chloro-dibenzo[b,d]pyran;
6H,6-aminomethyl-2-fluoro-dibenzo[b,d]pyran;
6H,6-aminomethyl-2-methoxy-dibenzo[b,d]pyran;
6H,6-aminomethyl-2-hydroxy-dibenzo[b,d]pyran;
6H,6-aminomethyl-1,10-dimethoxy-dibenzo[b,d]pyran;
6H,6-aminomethyl-8,9,10-trimethoxy-dibenzo[b,d]pyran;
6H,6-(2-methylamino-ethyl)-dibenzo[b,d]pyran;
6H,6-(3-methylamino-propyl)-dibenzo[b,d]pyran;
6H,6-(3-methylamino-propyl)-1-methoxy-dibenzo[b,d]pyran;
6H,6-(4-piperidinyl)-dibenzo[b,d]pyran;
6H,6-(1-hydroxy-2-tert-butylamino-ethyl)-dibenzo[b,d]pyran;
6H,6-(1-hydroxy-2-tert-butylamino-ethyl)-2-chloro-dibenzo[b,d]pyran;
6H,6-(1-hydroxy-2-tert-butylamino-ethyl)-2-methoxy-dibenzo[b,d]pyran;
6H,6-(1-hydroxy-2-tert-butylamino-ethyl)-1,10-dimethoxy-dibenzo[b,d]pyran;
6H,6-(1-hydroxy-2-tert-butylamino-ethyl)-8,9,10-trimethoxy-dibenzo[b,d]pyran,
and the pharmaceutically or veterinarily acceptable salts thereof.

5. 6H,6-(2-dimethylaminoethoxy-carbonyl)-dibenzo[b,d]-pyran, and the pharmaceutically or veterinarily acceptable salts thereof.

6. A pharmaceutical composition suitable for treatment or prevention of gastrointestinal ulcers in patients, comprising, as active principle, a pharmaceutically effective amount of a compound of formula (I) according to claim 1, or a pharmaceutically acceptable salt thereof, in association with a suitable carrier and/or diluent.

7. A pharmaceutical composition suitable for treating transplant reaction in patients arising from transplants of kidneys, heart, bone marrow, skin and endocrine glands, comprising, as an active principle, a therapeutically effective amount of a compound of formula (I) according to claim 1, or a pharmaceutically acceptable salt thereof, in association with a suitable carrier and/or diluent.

8. A pharmaceutical composition suitable for treating autoimmune disorders in patients arising from rheumatoid arthritis, systemic lupus erythematosus, glomerulonephritis, vasculitis and blood dyscrasias, comprising, as an active principle, a therapeutically effective amount of a compound of formula (I) according to claim 1, or a pharmaceutically acceptable salt thereof, in association with a suitable carrier and/or diluent.

9. A pharmaceutical composition suitable for treating bacterial and viral infections in patients, comprising, as an active principle, a therapeutically effective amount of the compound of formula (I) according to claim 1, or a pharmaceutically acceptable salt thereof, in association with a suitable carrier and/or diluent.

10. A pharmaceutical composition suitable for lowering the serum cholesterol and triglyceride level and/or increasing the total serum HDL cholesterol in patients, comprising, as an active principle, a therapeutically effective amount of a compound of formula (I) according to claim 1, or a pharmaceutically acceptable salt thereof, in association with a suitable carrier and/or diluent.

11. A method of treatment or prevention of gastrointestinal ulcers in a patient in need of such treatment, said method comprising administering to said patient an anti-ulcer effective amount of a compound of claim 1.

12. A method of treating transplant reaction in a patient arising from transplant of kidneys, heart, bone marrow, skin and/or endocrine glands, said method comprising administering to said patient an effective amount of a compound of claim 1.

13. A method of treating autoimmune disorders arising from rheumatoid arthritis, systemic lupus erythematosus, glomerulonephritis, vasculitis or blood dyscrasias, said method comprising administering to said patient an autoimmune effective amount of a compound of claim 1.

14. A method of treating bacterial and viral infections in a patient in need of such treatment, said method comprising administering to said patient an effective amount of a compound of claim 1.

15. A method of lowering the serum cholesterol and triglyceride level and/or increasing the total serum HDL cholesterol in a patient in need of such treatment, said method comprising administering to said patient an effective amount of a compound of claim 1.

* * * * *